US011155874B2

(12) United States Patent
Skog et al.

(10) Patent No.: US 11,155,874 B2
(45) Date of Patent: Oct. 26, 2021

(54) USE OF MICROVESICLES IN ANALYZING MUTATIONS

(71) Applicant: THE GENERAL HOSPITAL CORPORATION, Boston, MA (US)

(72) Inventors: Johan Karl Olov Skog, New York, NY (US); Xandra O. Breakefield, Newton, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 73 days.

(21) Appl. No.: 14/805,001

(22) Filed: Jul. 21, 2015

(65) Prior Publication Data
US 2015/0322532 A1 Nov. 12, 2015

Related U.S. Application Data

(63) Continuation of application No. 13/395,354, filed as application No. PCT/US2010/048310 on Sep. 9, 2010, now abandoned.

(60) Provisional application No. 61/241,020, filed on Sep. 9, 2009.

(51) Int. Cl.
C12Q 1/6886 (2018.01)
C12Q 1/6858 (2018.01)

(52) U.S. Cl.
CPC ......... *C12Q 1/6886* (2013.01); *C12Q 1/6858* (2013.01); *C12Q 2600/106* (2013.01); *C12Q 2600/118* (2013.01); *C12Q 2600/156* (2013.01)

(58) Field of Classification Search
CPC ............ C12Q 1/6858; C12Q 2527/125; C12Q 1/6886; C12Q 2600/106; C12Q 2600/118; C12Q 2600/156
USPC ....................................................... 435/91.2
See application file for complete search history.

(56) References Cited

U.S. PATENT DOCUMENTS

| | | |
|---|---|---|
| 5,219,727 A | 6/1993 | Wang et al. |
| 5,538,871 A | 7/1996 | Nuovo et al. |
| 5,547,859 A | 8/1996 | Goodman et al. |
| 5,556,773 A | 9/1996 | Yourno |
| 5,582,981 A | 12/1996 | Toole et al. |
| 5,639,606 A | 6/1997 | Willey |
| 5,639,611 A | 6/1997 | Wallace et al. |
| 5,811,250 A | 9/1998 | Solum |
| 5,840,867 A | 11/1998 | Toole et al. |
| 6,004,755 A | 12/1999 | Wang |
| 6,329,179 B1 | 12/2001 | Kopreski |
| 6,525,154 B1 | 2/2003 | Shea et al. |
| 6,607,898 B1 | 8/2003 | Kopreski et al. |
| 6,759,217 B2 | 7/2004 | Kopreski |
| 6,794,135 B1 | 9/2004 | Kopreski et al. |
| 6,812,023 B1 | 11/2004 | Lamparski et al. |
| 6,893,837 B2 | 5/2005 | Slamon et al. |
| 6,899,863 B1 * | 5/2005 | Dhellin ............... A61K 39/0011 424/1.21 |
| 6,913,879 B1 | 7/2005 | Schena |
| 6,916,634 B2 | 7/2005 | Kopreski |
| 6,939,671 B2 | 9/2005 | Kopreski |
| 6,994,960 B1 | 2/2006 | Foote et al. |
| 7,074,563 B2 | 7/2006 | Koster |
| 7,186,512 B2 | 3/2007 | Martienssen et al. |
| 7,198,893 B1 | 4/2007 | Koster et al. |
| 7,198,923 B1 | 4/2007 | Abrignani et al. |
| 7,332,533 B2 | 2/2008 | Kim et al. |
| 7,332,552 B2 | 2/2008 | Benicewicz et al. |
| 7,332,553 B2 | 2/2008 | Sellergren et al. |
| 7,364,848 B2 | 4/2008 | Van Beuningen et al. |
| 7,378,245 B2 | 5/2008 | Liu |
| 7,384,589 B2 | 6/2008 | Hart et al. |
| 7,671,010 B2 | 3/2010 | Arap et al. |
| 7,691,383 B2 | 4/2010 | Chakrabarty et al. |
| 7,776,523 B2 | 8/2010 | Garcia et al. |
| 7,807,183 B2 | 10/2010 | Hong et al. |
| 7,897,356 B2 * | 3/2011 | Klass ................... C12Q 1/6886 435/7.1 |
| 2002/0106684 A1 | 8/2002 | Kopreski |
| 2003/0077808 A1 | 4/2003 | Rosen et al. |
| 2005/0003426 A1 | 1/2005 | Ranum et al. |
| 2005/0250100 A1 | 11/2005 | Hayashizaki |
| 2006/0081516 A1 | 4/2006 | Hendrickson |
| 2006/0116321 A1 | 6/2006 | Robbins et al. |

(Continued)

FOREIGN PATENT DOCUMENTS

CA 2453198 A1 7/2005
CA 2676113 A1 1/2009

(Continued)

OTHER PUBLICATIONS

Miranda et al., International Society of Nephrology, 78, 191-199, (Year: 2010).*
Affymetrix, Apr. 20, 2001, Apr. 20, 2001, retrieved from the Internet on May 21, 2003. "Gene chip human genome U133 set."
Holdoff et al., "Analysis of circulating tumor dna to confirm sometic KRAS mutations", Journal of the National Cancer Institute, vol. 101 Issue 18, (2009).

(Continued)

Primary Examiner — Cynthia B Wilder
(74) Attorney, Agent, or Firm — David S. Resnick; Shayne Y. Huff; Nixon Peabody LLP

(57) ABSTRACT

Microvesicles are small membrane vesicles that either shed or bud off eukarotic cells. Analysis of the nucleic acid content of microvesicles may be useful in detecting the presence or absence of genetic aberrations. This invention discloses novel methods of diagnosing, prognosing, monitoring, or treating a disease, such as cancer, or other medical condition in a subject involving analyzing one or more nucleic acids contained within an isolated microvesicle for the presence or absence of one or more Kras genetic aberrations.

37 Claims, 9 Drawing Sheets

(56) References Cited

U.S. PATENT DOCUMENTS

| | | | |
|---|---|---|---|
| 2006/0160087 A1 | 7/2006 | McGrath et al. | |
| 2006/0223072 A1 | 10/2006 | Boyes et al. | |
| 2007/0104738 A1 | 5/2007 | Tatischeff et al. | |
| 2007/0105105 A1 | 5/2007 | Clelland | |
| 2007/0254351 A1 | 11/2007 | Abrignani | |
| 2007/0298118 A1 | 12/2007 | Lotvall et al. | |
| 2008/0268429 A1* | 10/2008 | Pietrzkowski | A61K 47/6901 435/6.18 |
| 2008/0287669 A1 | 11/2008 | Braman et al. | |
| 2009/0169636 A1 | 7/2009 | O'Hagan et al. | |
| 2009/0220944 A1 | 9/2009 | Fais et al. | |
| 2009/0227533 A1 | 9/2009 | Bader et al. | |
| 2010/0008978 A1 | 1/2010 | Drummond et al. | |
| 2010/0075315 A1 | 3/2010 | Pietrzkowski | |
| 2010/0184046 A1* | 7/2010 | Klass | C12Q 1/6886 435/7.1 |
| 2010/0196426 A1 | 8/2010 | Skog et al. | |
| 2010/0209355 A1 | 8/2010 | Chakrabarty et al. | |
| 2010/0255514 A1 | 10/2010 | Rak et al. | |
| 2011/0081651 A1* | 4/2011 | Hillan | A61K 31/517 435/6.14 |
| 2012/0142001 A1 | 6/2012 | Skog et al. | |
| 2012/0238467 A1 | 9/2012 | Taylor | |
| 2013/0040833 A1 | 2/2013 | Noerholm et al. | |

FOREIGN PATENT DOCUMENTS

| | | |
|---|---|---|
| CA | 2699646 A1 | 3/2009 |
| CN | 101085349 A | 12/2007 |
| JP | H08-509806 A | 10/1996 |
| JP | 2002521071 A | 7/2002 |
| JP | 2002535665 A | 10/2002 |
| JP | 2003514523 A | 4/2003 |
| JP | 2003531864 A | 10/2003 |
| JP | 2008501336 A | 1/2008 |
| JP | 2008035779 A | 2/2008 |
| JP | 2008509806 A | 4/2008 |
| JP | 2008541699 A | 11/2008 |
| JP | 2010534480 A | 11/2010 |
| JP | 2011510663 A | 4/2011 |
| JP | 5156829 B2 | 3/2013 |
| WO | 94/22018 A1 | 9/1994 |
| WO | 00/04194 A1 | 1/2000 |
| WO | 01/36601 A1 | 5/2001 |
| WO | 2001/082958 A2 | 11/2001 |
| WO | 02/099064 A2 | 12/2002 |
| WO | 03/023065 A1 | 3/2003 |
| WO | 03/050290 A2 | 6/2003 |
| WO | 03/076603 A2 | 9/2003 |
| WO | 2005/000098 A1 | 1/2005 |
| WO | 2005/000098 A3 | 1/2005 |
| WO | 2005/081867 A2 | 9/2005 |
| WO | 2005/121359 A1 | 12/2005 |
| WO | 2005/121369 A2 | 12/2005 |
| WO | 2006/020707 A2 | 2/2006 |
| WO | 2006/048291 A2 | 5/2006 |
| WO | 2006/048291 A3 | 5/2006 |
| WO | 2006/113590 A2 | 10/2006 |
| WO | 2007/015174 A2 | 2/2007 |
| WO | 2007/103572 A2 | 9/2007 |
| WO | 2007/126386 A1 | 11/2007 |
| WO | 2007/127848 A1 | 11/2007 |
| WO | 2008/084331 A2 | 7/2008 |
| WO | 2008/104543 A2 | 9/2008 |
| WO | 2009/015357 A1 | 1/2009 |
| WO | 2009/021322 A1 | 2/2009 |
| WO | 2009/030029 A1 | 3/2009 |
| WO | 2009/036236 A1 | 3/2009 |
| WO | 2009/092386 A2 | 7/2009 |
| WO | 2009/100029 A1 | 8/2009 |
| WO | WO 2009100029 * | 8/2009 |
| WO | 2009/155505 A2 | 12/2009 |
| WO | 2010/028099 A1 | 3/2010 |
| WO | 2010/056337 A2 | 5/2010 |
| WO | 2010/065968 A1 | 6/2010 |
| WO | 2010/099184 A1 | 9/2010 |
| WO | 2010/141955 A2 | 12/2010 |
| WO | 2011/009104 A1 | 1/2011 |
| WO | 2011/031877 A1 | 3/2011 |
| WO | 2011/031892 A1 | 3/2011 |
| WO | 2011/088226 A2 | 7/2011 |
| WO | 2011/127219 A1 | 10/2011 |
| WO | 2012/031008 A2 | 3/2012 |

OTHER PUBLICATIONS

Katoh et al., "Association of endogenous retroviruses and long terminal repeats with human disorders", Frontiers in Oncology 3(234)1-8 (2013).

Revenfeld et al., "Diagnostic and prognostic potential of extracellular vesicles in peripheral blood", Clin Ther. 36:830-846 (2014).

Yan et al., "IDH1 and IDH2 mutations in gliomas", N. Engl. J. Med., 360(8):765-773 (2009).

Carr et al., "Circulating membrane vesicles in leukemic blood", Cancer Res., 45:5944-5951 (1985).

Kang et al., "Mutational analysis of IDH1 codon 132 in glioblastomas and other common cancers", Int. J. Cancer, 125, pp. 353-355, (2009).

Kato et al., "A monoclonal antibody Imab-1 specifically recognizes IDH1R132H, the most common glioma-derived mutation", Biochemical and Biophysical Research Communications, 390, pp. 547-557 (2009).

Kosaka et al., "Circulating microRNA in body fluid: a new potential biomarker for cancer diagnosis and prognosis." Cancer Sci., 10(101):2087-2092 (2010).

Wang-Johanning et al., Cancer Res, 68(14):5869-5877 (2008). "Human Endogenous Retrovirus K Triggers an Antigen-Specific Immune Respone in Breast Cancer Patients".

Went, P.T., et al., "Frequent EpCam Protein Expression in Human Carcinomas", Hum Pathol., 35:122-128 (2004).

Wieckowski, E., and T.L. Whiteside, "Human Tumour-Derived vs Dendritic Cell-Derived Exosomes Have Distinct Biologic Roles and Molecular Profiles", Immunol Res., 36(1-3):247-254 (2006).

Wong, B.C., et al., "Circulating Placenta RNA in Maternal Plasma is Associated with a Preponderance of 5' mRNA Fragments: Implications for Noninvasive Prenatal Diagnosis and Monitoring", Clin Chem., 51:(10)1786-1795 (2005).

Wood, L.D., et al., "Genomic Landscapes of Human Breast and Colorectal Cancers", Science. 318:1108-1113 (2007).

Wright et al., Reviews in Urology, 9(4) 207-13 (2007) "Newer potential biomarkers in prostate cancer".

Yuan et al., PLoS One, 4(3):e4772 (2009). "Transfer of MicroRNAs by Embryonic Stem Cell Microvesicles."

Mack et al., "Transfer of the chemokine receptor CCR5 between cells by membrane-derived microparticles: A mechanism for cellular human immunodeficiency virus 1 infection", Nature Medicine, 6(7):769-775 (2000).

Maheswaran et al., The New England Journal of Medicine, 359(4)366-377 (2008). "Detection of Mutations in EGFR in Circulating Lung-Cancer Cells."

Mallardo, M., et al., "Isolation and characterization of Staufen-containing ribonucleoprotein particles from rat brain", Proc Natl Acad Sci U S A, 100(4):2100-2105 (2003).

Maron, J.L., , et al., "Gene expression analysis in pregnant women and their infants identifies unique fetal biomarkers that circulate in maternal blood", J Clin Invest., 117:3007-3019 (2007).

The Cancer Genome Atlas Research Network, Nature, 455:1061-1068 with Corrigendum (2008). "Comprehensive genomic characterization defines human glioblastoma genes and core pathways."

Miele et al., J. Mol. Biol. 171:281-295 (1983). "Autocatalytic Replication of Recomibinant RNA."

Millimaggi, D., et al., "Tumor Vesicle-Associated CD147 Modulates the Angiogenic Capability of Endothelial Cells", Neoplasia, 9(4):349-357 (2007).

Miranda et al., Kidney International, 78:191-199 (2010). "Nucleic acids within urinary exosomes/microvesicles are potential biomarkers for renal disease."

(56) References Cited

OTHER PUBLICATIONS

Myers et al., Science, 230:1242-6 (1985). "Detection of Single Base Substitutions by Ribonuclease Cleavage at Mismatch in RNA: DNA Duplexes."
Nagrath, S., et al., "Isolation of Rare Circulating Tumour Cells in Cancer Patients by Microchip Technology", Nature, 450(20/27):1235-1239 (2007).
Nakanishi et al., The Journal of Urology, 179:1804-1810 (2008). "PCA3 Molecular Urine Assay Correlates with Prostate Cancer Tumor Volume: Implications in Selecting Candidates for Active Surveillance."
Nakazawa et al., Proc. Natl. Acad. Sci. USA 91:360-364 (1994). "UV and skin cancer: Specific p53 gene mutation in normal skin as biologically relevant exposure measurement."
Ng, E. K., et al., "The Concentration of Circulating Corticotropin-releaslng Hormone mRNA in Maternal Plasma is Increased in Preeclamsia", Clin Chem. 49(5):727-731 (2003).
Ng, E.K., et al., "mRNA of placental origin is readily detectable in maternal plasma", Proc Natl Acad Sci U S A., 100(8):4748-4753 (2003).
Nilsson et al., British Jounral of Cancer 100(10):1603-1607 (2009). "Prostate cancer-derived urine exosomes: a novel approach to biomarkers for prostate cancer."
Noerholm et al., BMC Cancer, Biomed Central, 12(1): 22 (2012). "RNA Expression patterns in serum microvesicles from patients with gioblastoma multiforme and controls."
Novakova et al., Biochemical and Biophysical Research Communications, 386:1-5 (2009). "MircoRNA involvement in glioblastoma pathogenesis."
Orita et al., Proc. Natl. Acad Sci. USA, 86:2766-2770 (1989). "Detection of polymorphisms of human DNA by gel electrophoresis as single-strand conformation polymorphisms."
Ostrowski et al., Nature Cell Biology, 12(1):19-30 with Supplemental Information (2010). "Rab27a and Rab27b control different steps of the exosome secretion pathway."
Parsons, D.W., et al., "An Integrated Genomic Analysis of Human Glioblastoma Multiforme", Science, 321(5897):1807-1812 (2008).
Pelloski et al., "Epidermal Growth Factor Receptor Variant II Status Defines Clinically Distinct Subtypes of Glioblastoma", Journal of Clinical Oncology, 25(16):2288-2294 (2007).
Pisitkun et al., Molecular & Cellular Proteomics, 5:1760-1771 (2006). "Discovery of Urinary Biomarkers."
Pleasance et al., Nature, 463:191-197 (2010). "A comprehensive catalogue of somatic mutations from a human cancer genome."
Rak et al., Vnitr Lek. Mar. 2006:52 Suppl 1:135-8. "Genetic determinations of cancer coagulopathy, angiogenesis and disease progression."
Raposo et al., J. Exp. Med, 183:1161-1172 (1996) "B Lymphocytes Secrete Antigen-presenting Vesicles."
Ratajczak et al., Membrane-derived microvesicles: important and underappreciated mediators of cell-to-cell communication. Leukemia, 20:1487-1495 (2006).
Roman-Gomez et al., Leukemia Research, 32:487-490 (2008). Repetitive DNA hypomethylation in the advanced phase of chronic myeloid leukemia.
Ruprecht et al., Cell. Mol. Life Sci., 65:3366-3382 (2008). "Endogenous retroviruses and cancer."
Ryan et al., Gut, 52:101-106 (2003). "A prospective study of circulating mutant KRAS2 in the serum of patients with colorectal neoplasia: strong prognostic indicator in postoperative follow up."
Saal et al., Current Opinion in Nephrology and Hypertension 18:317-323 (2009). "MicroRNAS and the kidney: coming of age."
Sarbassov et al., Molecular Cell, 22:159-168 (2006). "Prolonged Rapamycin Treatment Inhibits mTORC2 Assembly and akt/PKB."
Schetter., A.J. et al., "Micro:RNA Expression Profiles Associated with Prognosis and Theraputic Outcome in Colon Adenocarcinoma", JAMA, 299(4):425-436 (2008).
Shinojima et al., Cancer Research 63(20) 6962-70 (2003) "Prognostic value of epidermal growth factor receptor in patients with glioblastoma multiforme."

Simons et al., Current Opinion in Cell Biology, 21:575-581 (2009). "Exosomes—vesicular carriers for intercellular communication."
Skog et al., Nature Cell Biology, 10(12):1470-1476 (2008). "Glioblastoma microvesicles transport RNA and proteins that promote tumour growth and provide diagnostics biomarkers."
Sliva et al., Virology Journal, 7:248 (2010). "Selective gene silencing by viral delivery of short hairpin RNA."
Srikantan et al., PNAS, 97(22):12216-12221 (2000). "PCGEM1, a prostate-specific gene, is overexpressed in prostate cancer."
Steemers et al., Nature Methods, 3(1):31-3 (2006). "Whole-genome genotyping with the single-base extension assay."
Stoorvogel et al., Traffic, 3:321-330 (2002). "The Biogenesis and Functions of Exosomes."
Tam, Jounral of Molecular Diagnostics, 10(5):411-414 (2008). "The Emergent Role of MircoRNAs in Molecular Diagnostics of Cancer."
Taylor et al., British Journal of Cancer, 92:305-3011 (2005). "Tumour-derived exosomes and their role in cancer-associated T-cell signallig defects."
Taylor et al., Gynecologic Oncology, 110:13-21 (2008). "MicroRNA signatures of tumour-derived exosomes as diagnostic biomarkers of ovarian cancer."
Tewes et al., Breast Cancer Res Treat, 115:581-590 (2009). "Molecular profiling and predictive value of circulating tumor cells in patients with metastatic breast cancer: an option for monitoring response to breast cancer related therapies."
Thery, C., et al., "Exosomes: Composition, Biogenesis and Function", Nat Rev. Immunol., 2:569-579 (2002).
Thery, C., et al., "Isolation and Characterization of Exosomes from Cell Culture Supernatants and Biological Fluids", Curr Protoc Cell Biol. Chapter 3:Unit 3 22.1-3.22.29, (2006).
Ting et al., Science, 331:593-596 (2011). "Aberrant Overexpression of Satellite Repeats in Pancreatic and Other Epithelial Cancers."
Valadi et al., Nature Cell Biology, 9(6):654-659 (2007). "Exosome-mediated of mRNAs and microRNAs is a novel mechanism of genetic exchange between cells."
Van Dijk et al., RNA, 13:1027-1035 (2007). "Human cell growth requires a functional cytoplasmic exosome, which is involved in various mRNA decay pathways."
Velculescu et al., Science, 270:484-7 (1995). "Serial Analysis of Gene Expression."
Voisset et al., Microbiol. Mol. Biol. Rev., 72(1):157-196 (2008). "Human RNA 'Rumor' Viruses: the Search for Novel Human Retroviruses in Chronic Disease."
Forbes et al., Nucleic Acids Research, 39(Database Issue):D945-D950 (2011). "COSMIC: mining complete cancer genomes in the Catalogue of Somatic Mutations in Cancer."
Furnari, F.B., et al., "Malignant Astrocytic Glioma: Genetics, Biology, and Paths to Treatment", Genes Dev., 21:2683-2710 (2007).
Geiss et al., Nature Biolotechnology 26(3):317-325 (2005) "Direct multiplexed measurement of gene expression with color-coded probe pairs."
Ginestra et al., "The Amount and Proteolytic Content of Vesicles Shed by Human Cancer Cell Lines Correlates with their in Vitro Invasiveness", Anticancer Research. 18:3433-3438 (1998).
Golan et al., Neoplasia, 10(6):521-533 (2008). "Human Endogenous Retrovirus (HERV-K) Reverse Transriptase as a Breast Cacncer Prognostic Marker."
Gonzales et al., Nephrol Dial Transplant 23:1799-1801 (2008). "Urinary exosomes: is there a future?"
Goodier et al., Cell, 135:23-35 (2003). "Retrotransposons Revisted: The Restraint and Rehabilitation of Parasites."
Gormally, E., et al., "Circulating Free DNA in Palsma or Serum as Biomarker of Carcinogenesis: Practical Aspects and Biological Significance", Mutat Res., 635:105-117 (2007).
Greco, V., et al., "Argosomes.: A Potential Vehicle for the Spread of Morphogens through Epithelia", Cell., 106:633-645 (2001).
Green et al., Blood, 116(15):2779-2782 with supplemental material (2010). "The Prognostic significance of IDH1 mutations in younger adult patients with acute myleoid leukemia is dependent on FLT3/IDT status."

(56) References Cited

OTHER PUBLICATIONS

Groskopf, J., et al., "APTIMA PCA3 Molecular Urine Test: Development of a Method to Aid in the Diagnosis of Porstate Cancer", Clin Chem., 52(6):1089-1095 (2006).

Guatelli et al, Proc. Natl. Acad. Sci. USA, 87:1874-1878 (1990). "Isothermal. in vitro amplification of nucleic acids by a multienzyme reaction modeled after retroviral replication."

Guescini et al., J Neural Transm, 117:1-4 (2010). "Astrocytes and Glioblastoma cells release exosomes carrying mtDNA."

Hahn, Bioessays, 15(7):477-484 (1993). "Molecular Biology of Double-Minute Chromosomes."

Hanahan et al., Cell, 100:57-70 (2000). "The Hallmarks of Cancer."

Hartmann et al., Acta Neuropathol, 120:707-718 (2010). "Patients with IDHI wild type anaplastic astrocytomas exhibit worse prognosis than IDH1-mutated glioblastomas, and IDH1 mutation status accounts for the unfavorable prognostic effect of higher age: implications for classification of gliomas."

Heimberger et al., J Transl Med. Oct. 19, 2005;3:38. "The Natural History of EGFR and EGFRvIII in glioblastoma patients."

Hessels et al., European Urology., 44:8-16 (2003). "DD3PCA3-based Molecular Urine Analysis for the Diagnosis of Prostate Cancer."

Hessels et al., Clin Cancer Res 13:5103-5108 (2007). "Detection of TMPRSS2-ERG Fusion Transcripts and Prostate Cancer Antigen 3 in Urinary Sediments May Improve Diagnosis of Prostate Cancer."

Hildebrandt et al., Jounral of Clinical Oncology, 27(6):857-871 (2009). "Genetiv Variations in the P13K/PTEN/AFT/mTOR Pathway are Associated With Clinical Outcomes in Esophageal Cancer Patients Treated with Chemoradiotherapy."

Hunter et al., PLoS ONE, 3(11)e3694 (2008). "Detection of microRNA Expression in Human Peripheral Blood Microvesicles."

Hero et al., Cell Death and Differentiation, 15:80-88 (2008). "Tumour-released exosomes and their implications in cancer imunity."

Iorio et al., Cancer Research, 67(18):8699-8707 (2007). "microRNA signatures in human ovarian cancer."

Itadani et al., Current Genomics, 9:349-360 (2008). "Can Systems Biology Understand Pathway Activation? Gene Expression Signatures as Surrogate Markers for Understanding the Complexity of Pathway Activation."

Janowska-Wieczorek, A., et al., "Microvesicles derived from activated platelets induce matastasis and angiogenesis in lung cancer", Int J Cancer., 113:752-760 (2005).

Johnson, S., et al., "Surface-Immobilizaed Peptide Aptamers as Probe Molecules for Protein Detection", Anal Chem., 80:978-983 (2008).

Ji et al., Oncogene, 22:8031-8041 (2003). "MALAT-1, a novel noncoding RNA, and thymosin β4 predict metastasis and survival in early-stage non-small cell lung cancer."

Jones, S., et al., "Core Signaling Pathways in Human Pancreatic Cancers Revealed by Global Genomic Alanyses", Science, 321(5897):1810-1806 (2008).

Kan et al., The Lancet, 2:910-2 (1978). "Antenatal Diagnosis of Sickle-Cell Anaemia by D.N.A. Analysis of Amniotic-Fluid Cells."

Kan et al, Proc. Natl. Acad. Sci. USA, 75(11):5631-5635 (1978). "Polymorphism of DNA sequence adjacent to human β-globlin structural gene. Relationship to sickle mutation."

Keller et al., Kdney International, 72:1095-1102 (2007) "CD24 is a marker of exosomes secreted into urine and amniotic fluid."

Kislauskis, E.H., et al., "Sequences Responsible for Intracellular Localization of beta-Actin Messenger RNA Also Affect Cell Phenotype", J Cell Biol., 127:441-451 (1994).

Kleiman et al., Int. J. Cancer, 110:459-461 (2004). "HERV-K(HML-2) GAG/ENV Antibodies as Indicator for Therapy Effect in Patients with Germ Cell Tumors."

Klein et al., Nature Biotechnology, 20:387-392 (2002). "Combined transcriptome and genome analysis of single microstatic cells."

Klemke et al., The Journal of Cell Biology, 137(2):481-492 (1997). "Regulation of Cell Motility by Mitogen-activated Protein Kinase."

Koga et al., Anticacer Research, 25:3703-3707 (2005). "Purification, Characterization and Biological Significance of Tumor-derived Exosomes."

Kristensen et al., Clinical Chemistry, 55(8):1471-1483 (2009). "PCR-Based Methods for Detecting Single-Locus DNA Methylation Biomarkers in Cancer Diagnostics, Prognostics, and Responce to Treatment."

Krupp, G. "Stringent RNA quality control using the Agilent 2100 bioanalyzer" Application Note, Agilent Technologies, Feb. 1, 2005.

Kwoh et al., Proc. Natl. Acad. Sci. USA 86:1173-1177 (1989). "Transcription-based amplification system and defection of amplified human immunodeficiency virus type 1 with a bead-based sandwich hybridization format."

Landegren et al., Science, 241:1077-1080 (1988). "A Ligase-Mediated Detection Technique."

Laxman et al., Cancer Research, 68:645-649 (2008). "A first-generation multiplex biomarker analysis of urine for the early detection of prostate cancer."

Lee et al., PLoS One, 6(6):e21300 (2011). "microRNA expression and clinical outcome of small cell lung cancer."

Li et al., Natute Medicine, 14(5) 579-584 (2008). "Replacing PCR with COLD-PCR enriches variant DNA sequences and redefines the sensitivity of genetic testing."

Liu et al., 127:1223-1237 (2006). "Reconstitution, Activities and Structure of the Eukaryotic RNA Exosome."

Liu, C., et al., "Murine Mammary Carcinoma Exosomes Promote Tumor Growth by Suppression of NK Cell Function", J Immunol, 176:1375-1385 (2006).

Lo et al., Nature Reviews Genetics, 8:71-77 (2007). "Prenatal Diagnosis: progress through plasma nucleic acids."

Lo, Y.M., et al., "Plasma placental RNA allelic ratio permits noninvasive prenatal chromosomal aneuploidy detection", Nat Med., 13(2):218-223 (2007).

Lo et al., Cytometry Part A, 73A:321-322 (2008). "Automated Gating of Flow Cytomerty Data via Robust Model-Based Clustering."

Lower et al., Proc. Natl. Acad. Sci., 93:5177-5187 (1996). "The viruses in all of us: Characteristics and biological significance of human endogenous retrovirus sequences."

Abravaya et al., Nucleic Acids Research, 23(4):675-682 (1995). "Detection of point mutations with a modified ligase chain reaction (Gap-LCR)."

Alessi et al., Sci. Signal., 2(67):pe27 (2009). "New Insights into mTOR Signaling: mTORC2 and Beyond."

Allawi et al., "Quatitation of microRNAs using a modified Invader assay", RNA, 10:1153-1161 (2004).

Al-Nedawi et al., Nature Cell Biology, 10(5):619-624 (2008). "Intercellular transfer of the oncogenis receptior EGFRvIII by microvesicles derived from tumour cells."

Ason et al., PNAS, 103(39):14385-14389 (2006). "Differences in vertebrate microRNA expression."

Baj-Krzyworzeka et al. Cancer Immunology, Immunotherapy, 55(7):808-818 (2006). "Tumour-derived microvesicles carry several surface determinants and mRNA of tumour cells and transfer some of these determinants to monocytes."

Balzar et al., J Mol Med, 77:699-713 (1999). "The biology of the 17-1A antigen (Ep-CAM)."

Bamford et al., British Journal of Cancer, 9(12):355-358 (2004). "The COSMIC (Catalogue of Somatic Mutations in Cancer) database and website."

Benner et al., Trends in Genetics, 17:414-418 (2001). "Evolution, language and analogy in functional genomics."

Bergsmedh et al., PNAS, 98(11):6407-6411 (2001). "Horizontal transfer of oncogenes by uptake of apoptotic bodies."

Booth et al., "Exosomes and HIV Gag bud from endosome-like domains of the T cell plasma membrane", J Cell Biol., 172(6):923-935 (2006).

Bossi et al., "Molecularly imprinted polymers for the recognition of proteins: The State of the art", Biosensors Bioelectronics, 22:1131-1137 (2007).

Bratthauer et al., Cancer, 73(9):2333-2336 (1994). "Expression of LINE-1 Retrotransposons in Human Breast Cancer."

(56) References Cited

OTHER PUBLICATIONS

Burghoff et al., Cardiovascular Research, 77:534-543 (2008). "Horizontal gene transfer from human endotheilial cells to rat cardiomyocytes after intracoronary transplantation."
Cadieux et al., Cancer Res, 66:8469-8476 (2006). "Genome-wide Hypomethylation in Human Glioblastomas Associated with Specific Copy Number Alteration Methylenetetrahydrofolate Reductase Allele Sstatus, and Increased Proliferation."
Cermelli et al., PLoS ONE, 6(8):e23937 (2011). "Circulating microRNAs in patients with chronic hepatitis C and non-alcoholic fatty liver disease."
Chaput et al., "The Potential of Exosomes in Immunotherapy", Expert Opin Biol Ther., 5(6):737-747 (2005).
Chen et al., Nucleic Acid Research, 33(20):e179 (2005). "Real-time quantification of microRNAs by stem-loop RT-PCR."
Chen et al., Cell Research, 18:997-1006 (2008). "Characterization of microRNAs in serum: a novel class biomarkers for diagnosis of cancer and other diseases."
Chen et al., Lab Chip, 10:505-511 (2010). "Microfluidic isolation and transcriptome analysis of serum microvesicles."
Cheng et al., Current Cancer Drug Targets, 8:2-6 (2008). "Advnces of AKT Pathway in Human Oncogenesis and as a Target for Anti-Cancer Drug Discovery."
Cheruvanky et al., Am J Physiol Renal Physiol, 292:F1657-F1661 (2007). "Rapid isolation of urinary exosomal biomarkers using a nanomembrane ultrafiltratoin concentrator."
Cheung et al., Nature Genetics, 33:422-425 (2003). "Natural variation of in human gene expression assessed in lymphoblastoid cells."
Cho et al., J Pathol, 211:269-277 (2007). "Hypermethylation of CpG island loci and hypomethylation of LINE-I and Alu repeats in prostate adenocarcinoma and their relationship to clinicopathological features."
Ciafre et al., Biochemical and Biophysical Research Communications, 334:1351-1358 (2005). "Extensive modulation of a set of microRNAs in primary glioblastoma."
Clayton et al., "Human Tumor-Derived Exosomes Selectively Impair Lymphocyte Responses to Interleukin-2" Cancer Res., 67(15):7458-7466 (2007).
Cocucci et al., Trends Cell Biol, 19:43-51 (2009). "Shedding microvesicles: artefacts no more."
Contreras-Galindo et al., Jounral of Virology, 82(19):9329-9336 (2008). "Human Endogenous Retrovirus K (HML-2) Elements in the Plasma of People with Lymphoma and Breast Cancer."
Corsten et al., Circulation Cardiovascular Genetics, 2:499-506 (2010). "Circulating mircoRNA-208b and microRNA-499 reflect myocardial damage in cardiovascular disease."
Cortez et al., Expert Opin. Biol. Ther., 9(6):703-711 (2009). "MircoRNA identification in plasma and serum: a new tool to diagnose and monitor diseases."
Cotton et al., Proc. Natl. Acad. Sci. USA, 85:4397-4407 (1988). "Reactivity of cytosine and thymine in single-base-pair mismatches with hydroxylamine and osmium tetroxide and its application to the study of mutations."
Cowell et al., Mircoarray Analysis of the Physical Genome: Methods and Protocols, 556:47-65 (2009). "Application of Oligonucleotides Arrays for Coincident Comparative Genomic Hybridization, Ploidy Status and Loss of Heterozygosity Studies in Human Cancers."
Daskalos et al., Int. J. Cancer, 124:81-87 (2009). "Hypomethylation of retrotransposable elements correlates with genomic instability in non-small cell lung cancer."
Day el al., Cancer Letters, 301:1-6 (2011). "PCA3: From basic molecular science to the clinical lab."
Deregibus et al., Blood, 110(7):2440-2448 (2007). "Endothelial progenitor cell-derived microvesicles activate and angiogenic program in endothelial cells by a horizontal transfer of mRNA."
Diehl et al., Nature Methods, 3(7):551-559 with supplemental material (2006). "BEAMing: single-molecules PCR on Microparticles in water-in-oil emulsions."
Diehl et al., "Circulating mutant DNA to assess tumor dynamics", Nat Med., 14(9):985-990 (2008).
Dowling et al., Science, 328:1172-1176 (2010). "mTORC1-Mediated Cell Proliferation, But Not Cell Growth, Controlled by the 4E-BPs."
Dressman et al., PNAS 100(15):8817-8822 (2003). "Transforming single DNA molecules into fluorescent magnetic particles for detection and enumeration of genetic variations."
Duijvesz et al., European Urology, 59(5):823-831 (2011). "Exosomes as biomarker treasure chests for prostate cancer."
El-Hefnawy Talal et al., Clinical Chemistry, 50(3):564-573 (2004). "Characterization of amplifiable, circulating RNA in plasma and its potential as a tool for cancer diagnostics."
Estecio et al, PLoS One, 5:e399 (2007). "Line-1 Hypomethylation in Cancer is Highly Variable and Inversly Correlated with Microsatellite Instability."
Fabbri et al., "MicroRNA-29 family reverts aberrant methylation in lung cancer by targeting DNA methyltransferases 3A and 3B", PNAS, 104(40)15805-15810 (2007).
Fiorentino et al., Molecular Human Reproduction, 9(7):399-410 (2003). "The minisequencing method: an alternnative strategy for preimplantation genetic diagnosis of single gene disorders."
Fischer et al., Methods in Enzymology, 68:183-91 (1979). "Two-Dimensional Electrophoretic Separation of Restriction Enzyme Fragments of DNA."
Fischer et al., Cell, 16:191-200 (1979). "Length-Independant Separation of DNA Restriction Fragments in Two-Dimensional Gel Electrophoresis."
Forbes et al., Current Protocols in Human Genetics, Supplement 57:10.11.1-10.11.26 (2008). "The Catalogue of Somatic Mutations in Cancer (COSMIC)."
Forbes et al., Nucleic Acids Research, 38(Database issue):D652-657 (2010). "COSMIC (the Catalogue of Somatic Mutations in Cancer): a resource to investigate acquired mutations in human cancer."
Oliveira et al., Human Molecular Genetics, 13(19):2303-2311 (2004). "Distinct patterns of KRAS mutations in colorectal carcinomas according to germilne mismatch repair defects and hMLH1 methylation status."
Yu, J.Y. et al. "Oncogenic events regulating tissue factor expression," Haematologica Reports 1(9):18-20 (2005).
Gambim et al., "Platelet-derived exosomes induce endothelial cell apoptosis through peroxynitrite generation: experimental evidence for a novel mechanism of septic vascular dysfunction", Crit Care 11(5) R107 (2007).
GenBank (Accession NM_005896 submitted Jan. 31, 2003).
Biernat et al., "Predominant expression of mutant EGFR (EGFRvIII) is rare in primary glioblastomas", Brain Pathol 14(2) 131-136 (2004).
Chabert et al., "Cell culture of tumors alters endogenous poly(ADPR)polymerase expression and activity", Int J Cancer 53(5) 837-842 (1993).
Choi et al., "Proteomic analysis of microvesicles derived from human colorectal cancer ascites.", Proteomic 11(13) 2745-2751 (2011).
Cooperberg et al., "The changing face of low-risk prostate cancer: trends in clinical presentation and primary management", J Clin Oncol 22(11) 2141-9 (2004).
Dermer "Another anniversary for the war on cancer." Nature Biotechnology 12(3):320 (1994).
Diehl et al., "Detection and quantification of mutations in the plasma of pateitns with colorectal tumors" PNAS 102(45) 16268-16373 (2005).
Eastham et al., "Relationship between clonogenic cell survival, DNA damage and chromosomal radiosensitivity in nine human cervix carcinoma cell lines" Int. Journal Radiat. Biol 77(3) 295-302 (2001).
Keller et al., "Exosomes: from biogenesis and secretion to biological function", Immunol Lett 107(2) 102-8 (2006).
May "How Many Species Are there on Earth?", Science 241(1) 1441-1449 (1998).

(56) References Cited

OTHER PUBLICATIONS

Mellinghoff et al., "Molecular determinants of the response of glioblastomas to EGFR kinase inhibitors", N Engl J Med 353(19) 2012-2024 (2005).
Mitchell et al., "Can urinary exosomes act as treatment response markers in prostate cancer?", J Transl Med 7:4 (2009).
Moderk et al., "Genome-wide detection of alternatives splicing in expressed sequences of human genes", Nucleic Acids Research 29(13) 2850-2859 (2001).
Moscatello et al., "Frequent expression of a mutant epidermal growth factor receptor in multiple human tumors", Cancer Res 55(23) 5536-5539 (1995).
Nishikawa et al., "Immunohistochemical analysis of the mutant epidermal growth factor, deltaEGFR, in glioblastoma" Brain Tumor Pathol 21(2) 53-56 (2004).
Ruprecht et al., "Human endogenous retrovirus family HERV-K(HML-2) RNA transcripts are selectively packaged into retroviral particles produced by the human germ cell tumor line Tera-1 and originate mainly from a provirus on chromosome 22q11.21" J Virol 82(20) 10008-10016 (2008).
Saito-Hisaminto et al., "Genome-Wide Profiling of Gene Expression in 29 Normal Human Tissues with cDNA Microarray", DNA Research 9 35-45 (2002).
Schmidt et al., "Quantitative multi-gene expression profiling of primary prostate cancer", Prostate 66(14) 1521-34 (2006).
Singh et al., "Gene Expression correlates of clinical prostate cancer behavior", Cancer Cell 1(2) 203-209 (2002).
The International SNP Map Working Group., "A map of human genome sequence variation containing 1.42 million single nucleotide polymorphisms" Nature 409 928-933 (2001).
Tomlins et al., "Recurrent fusion of TMPRSS2 and ETS transcription factor genes in prostate cancer", Science 310(5748) 644-648 (2005).
Yoshimoto et al., "Development of a real-time RT-PCR assay for detecting EGFRvIII in glioblastoma samples", Clin Cancer Res 14(2) 488-493 (2008).
Yu et al., "Shedding of tissue factor (TF)-containing microparticles rather than alternatively spliced TF is the main source of TF activity released from human cancer cells", J Throm Haemost 2(11) 2065-2067 (2004).
Bess et al., "Microvesicles are a source of contaminating cellular proteins found in purified HIV-1 preparations." Virology 230(1):134-144 (1997).
Grant et al., "The proteins of normal urine." Journal of Clinical Pathology 10(4):360-367 (1957).
Tullis et al., "Calcium protects DNase I from proteinase K: a new method for the removal of contaminating RNase from DNase I." Analytical Biochemistry 107(1):260-264 (1980).
Johnstone. "Exosomes biological significance: A concise review." Blood Cells, Molecules, and Diseases 36(2): 315-321 (2006).
Lotvall at al. "Cell to Cell Signalling via Exosomes Through esRNA." Cell Adhesion & Migration 1(3): 156-158 (2007).
Perkel. "Finding Points to Possible Blood Test for Brain Tumors." HealthDay News [retrieved Apr. 18, 2019] https://www.medicinenet.com/script/main/art.asp?articlekey=94287 1-3 (2008).
Halatsch et al. "Epidermal growth factor receptor inhibition for the treatment of the glioblastoma multiforme and other malignant brain tumors." Cancer Treatment Reviews, 32: 74-89, (2006).
Schalken "Validation of molecular targets in prostate cancer." BJU International, 96: 23-29 (2005).
Huang et al. "Optimization of DNase I Removal of Contaminating DNA from RNA for Use in Quantitative RNA-PCR." Biotechniques 20(6): 1012-1020 (1996).
Smalheiser. "Exosomal transfer of proteins and RNAs at synapses in the nervous system." Biology Direct 2(1): 1-15 (2007).

\* cited by examiner

USE OF MICROVESICLES IN ANALYZING MUTATIONS

CROSS REFERENCE TO RELATED APPLICATIONS

This Application is a Continuation Application of U.S. application Ser. No. 13/395,354, which is a 35 U.S.C. 371 National Stage entry of International Application No. PCT/US2010/048310, filed Sep. 9, 2010, which designates the United States, and which claims the benefit under 35 U.S.C. § 119(e) of U.S. Provisional Application No. 61/241,020, filed Sep. 9, 2009, the contents of each of which are incorporated herein by reference in their entirety.

FIELD OF THE INVENTION

The present invention relates to the fields of medical diagnosis, and prognosis, patient monitoring, treatment efficacy, and molecular diagnostics based on the analysis of Kras nucleic acids extracted from microvesicles.

BACKGROUND

Molecular diagnostics, used to diagnose, monitor, treat, and evaluate diseases and other medical conditions, is becoming an increasingly important tool, particularly with the accumulating knowledge of the molecular mechanisms underlying various types of diseases and medical conditions. Molecular diagnostics is particularly valuable in the context of cancer, since our knowledge of the underlying genetic causes of cancers is rapidly expanding.

Cancers arise through accumulation of genetic alterations that promote unrestricted cell growth. It has been stated that each tumor harbors, on average, around 50-80 mutations that are absent in non-tumor cells (Jones et al., 2008; Parsons et al., 2008; Wood et al., 2007). One family of oncogenes that is commonly mutated in cancers is the RAS family. During tumorigenesis, aberrant Ras signaling can lead to uncontrolled cell proliferation and resistance to apoptosis. Moreover, Ras has been shown to play an important role in the expression of matrix metalloproteinases, as well as other processes that promote tumor invasion and metastasis. Of the members of the Ras family, which includes the Hras, Kras, and Nras genes, Kras is most commonly mutated in cancers.

Current technologies to detect genetic mutations include the analysis of biopsy samples and the non-invasive analysis of mutant tumor DNA fragments circulating in bodily fluids, such as blood (Diehl et al., 2008). The former method is invasive, complicated, possibly harmful to subjects, and not particularly sensitive. The latter method inherently lacks sensitivity due to extremely low copy number of mutant cancer DNA in bodily fluid (Gormally et al., 2007). Therefore, one challenge facing cancer diagnosis is to develop a diagnostic method that can detect tumor cells at different stages non-invasively, yet with high sensitivity and specificity.

This invention discloses novel methods of diagnosing, prognosing, monitoring, and treating a disease, such as cancer, or other medical condition in a subject involving the analysis of one or more nucleic acids contained within one or more microvesicles isolated from a bodily fluid sample for the presence or absence of one or more Kras genetic aberrations.

BRIEF SUMMARY OF THE INVENTION

One aspect of the invention are methods for detecting the presence or absence of a Kras genetic aberration in a fluid sample, the methods comprising the steps of: (a) isolating one or more microvesicles from a fluid sample; and (b) analyzing one or more nucleic acids contained within the one or more microvesicles for the presence or absence of a Kras genetic aberration.

Another aspect of the invention are diagnostic or prognostic methods, wherein said methods aid in the diagnosis or prognosis of a disease or other medical condition in a subject, the methods comprising the steps of: (a) isolating one or more microvesicles from a body fluid sample from the subject; and (b) analyzing one or more nucleic acids contained within the one or more microvesicles for the presence or absence of a Kras genetic aberration associated with the diagnosis or prognosis of a disease or other medical condition.

A further aspect of the invention are monitoring methods, wherein said methods aid in monitoring the status of a disease or other medical condition in a subject over time, the methods comprising the steps of: (a) isolating one or more microvesicles from a body fluid sample from the subject: (b) analyzing one or more nucleic acids contained within the one or more microvesicles for the presence or absence of a Kras genetic aberration associated with the disease or other medical condition; and (c) repeating steps (a) and (b) after the passage of an interval of time.

Another aspect of the invention are evaluation methods, wherein said methods aid in evaluating treatment efficacy in a subject having a disease or other medical condition, the methods comprising the steps of: (a) isolating one or more a microvesicles from a body fluid sample from the subject; and (b) analyzing one or more nucleic acids contained within the one or more microvesicles for the presence or absence of a Kras genetic aberration associated with treatment efficacy for the disease or other medical condition.

In certain embodiments of the foregoing aspects of the invention, the methods may further comprise the step of treating the one or more isolated microvesicles with DNase prior to analysis to eliminate all or substantially all of any DNA located on the surface of the one or more microvesicles or outside of the one or more microvesicles.

In certain preferred embodiments of the foregoing aspects of the invention, the Kras genetic aberration is selected from the group consisting of: G12A, G12D, G12R, G12C, G12S, G12V, or G13D.

In certain preferred embodiments of the foregoing aspects of the invention, the disease or other medical condition is cancer. Particularly, preferred cancers are colorectal, pancreatic, thyroid, lung, acute myeloid leukemia, or glioblastoma.

In certain preferred embodiments of the foregoing aspects of the invention, the body fluid is blood, plasma, serum, urine, or combinations thereof. In certain preferred embodiments of the foregoing aspects of the invention, the subject is a human.

In certain preferred embodiments of the foregoing aspects of the invention, the microvesicles isolated from a bodily fluid are enriched for those originating from a specific cell type, such as specific cell type is lung, pancreas, stomach, intestine, bladder, kidney, ovary, testis, skin, colorectal, breast, prostate, brain, esophagus, liver, placenta, or fetus cells.

In certain embodiments of the foregoing aspects of the invention, microvesicular surface molecules are used to enrich for microvesicles from a specific cell. In certain embodiments, the microvesicular surface molecules are surface antigens associated with tumor cells, such as epithelial-cell-adhesion-molecule (EpCAM), CD24. CD70, carcinoembryonic antigen (CEA), EGFR, EGFRvIII and other variants, Fas ligand, TRAIL, transferrin receptor, p38.5, p97, or HSP72.

In certain embodiments of the foregoing aspects of the invention, the absence of a microvesicular surface molecule is used to enrich for microvesicles from a specific cell type, such as the surface molecules CD80 or CD86.

In certain embodiments of the foregoing aspects of the invention, the isolation of microvesicles from a specific cell type is accomplished by using antibodies, aptamers, aptamer analogs, or molecularly imprinted polymers.

In certain embodiments of the foregoing aspects of the invention, one or more nucleic acids are extracted from the one or more microvesicles prior to analysis.

In certain embodiments of the foregoing aspects of the invention, the nucleic acids are DNA.

In certain embodiments of the foregoing aspects of the invention, the nucleic acids are RNA. In some embodiments, the RNA are reverse-transcribed into complementary DNA.

In certain embodiments of the foregoing aspects of the invention, the nucleic acids are analyzed directly without an amplification step.

In other embodiments of the foregoing aspects of the invention, the nucleic acids are amplified prior to analysis. In some embodiments, the nucleic acid amplifications are carried out by polymerase chain reaction (PCR) and its variants such as in situ PCR, quantitative PCR, nested PCR; self-sustained sequence replication and its variants; transcriptional amplification system and its variants; Qb Replicase and its variants: or cold-PCR.

In other embodiments of the foregoing aspects of the invention, the subject is a human colorectal cancer patient.

The present invention may be as defined in any one of the following numbered paragraphs.

1. A method for detecting the presence or absence of a Kras genetic aberration in a fluid sample, the method comprising the steps of:
   (a) isolating one or more microvesicles from a fluid sample; and
   (b) analyzing one or more nucleic acids contained within the one or more microvesicles for the presence or absence of a Kras genetic aberration.
2. A diagnostic or prognostic method, wherein said method aids in the diagnosis or prognosis of a disease or other medical condition in a subject, the method comprising the steps of:
   (a) isolating one or more microvesicles from a body fluid sample from the subject; and
   (b) analyzing one or more nucleic acids contained within the one or more microvesicles for the presence or absence of a Kras genetic aberration associated with the diagnosis or prognosis of a disease or other medical condition.
3. A monitoring method, wherein said method aids in monitoring the status of a disease or other medical condition in a subject over time, the method comprising the steps of:
   (a) isolating one or more microvesicles from a body fluid sample from the subject;
   (b) analyzing one or more nucleic acids contained within the one or more microvesicles for the presence or absence of a Kras genetic aberration associated with the disease or other medical condition; and
   (c) repeating steps (a) and (b) after the passage of an interval of time.
4. An evaluation method, wherein said method aids in evaluating treatment efficacy in a subject having a disease or other medical condition, the method comprising the steps of:
   (a) isolating one or more a microvesicles from a body fluid sample from the subject; and
   (b) analyzing one or more nucleic acids contained within the one or more microvesicles for the presence or absence of a Kras genetic aberration associated with treatment efficacy for the disease or other medical condition.
5. The method of any of paragraphs 1-4, further comprising the step of treating the one or more isolated microvesicles with DNase prior to analysis to eliminate all or substantially all of any DNA located on the surface of the one or more microvesicles or outside of the one or more microvesicles.
6. The method of any of paragraphs 1-5, wherein the Kras genetic aberration is selected from the group consisting of: G12A, G12D, G12R, G12C, G12S, G12V, or G13D.
7. The method of any of paragraphs 1-6, wherein the disease or other medical condition is cancer.
8. The method of paragraph 7, wherein the cancer is colorectal, pancreatic, thyroid, lung, acute myeloid leukemia, or glioblastoma.
9. The method of any of paragraphs 1-8, wherein the body fluid is blood, plasma, serum, urine, or combinations thereof.
10. The method of any of paragraphs 1-9, wherein the subject is a human.
11. The method of any of paragraphs 1-10, wherein the microvesicles isolated from a bodily fluid are enriched for those originating from a specific cell type.
12. The method of paragraph 11, wherein the specific cell type is lung, pancreas, stomach, intestine, bladder, kidney, ovary, testis, skin, colorectal, breast, prostate, brain, esophagus, liver, placenta, or fetus cells.
13. The method of paragraph 11 or 12, wherein a microvesicular surface molecule is used to enrich for microvesicles from a specific cell type.
14. The method of paragraph 13, wherein the microvesicular surface molecule is a surface antigen associated with tumor cells.
15. The method of paragraph 14, wherein the microvesicular surface molecule is epithelial-cell-adhesion-molecule (EpCAM), CD24, CD70, carcinoembryonic antigen (CEA), EGFR, EGFRvIII and other variants, Fas ligand, TRAIL, transferrin receptor, p38.5, p97, or HSP72.
16. The method of paragraph 11, wherein the absence of a microvesicular surface molecule is used to enrich for microvesicles from a specific cell type.
17. The method of paragraph 16, wherein the absent surface molecule is CD80 or CD86.
18. The method of any of paragraphs 11-17, wherein the isolation of microvesicles from a specific cell type is accomplished by using antibodies, aptamers, aptamer analogs, or molecularly imprinted polymers.
19. The method of any of paragraphs 1-18, wherein the one or more nucleic acids are extracted from the one or more microvesicles prior to analysis.
20. The method of any of paragraphs 1-19, wherein the nucleic acid is DNA.
21. The method of any of paragraphs 1-20, wherein the nucleic acid is RNA.
22. The method of paragraph 21, wherein the RNA is reverse-transcribed into complementary DNA.

23. The method of any of paragraphs 1-22, wherein the nucleic acid is analyzed directly without an amplification step.
24. The method of any of paragraphs 1-22, wherein the nucleic acid is amplified prior to analysis.
25. The method of paragraph 24, wherein the nucleic acid amplification is carried out by polymerase chain reaction (PCR) and its variants such as in situ PCR, quantitative PCR, nested PCR; self-sustained sequence replication and its variants; transcriptional amplification system and its variants; Qb Replicase and its variants; or cold-PCR.
26. The method of any of paragraphs 1-25, wherein the subject is a human colorectal cancer patient.

Figure 1:
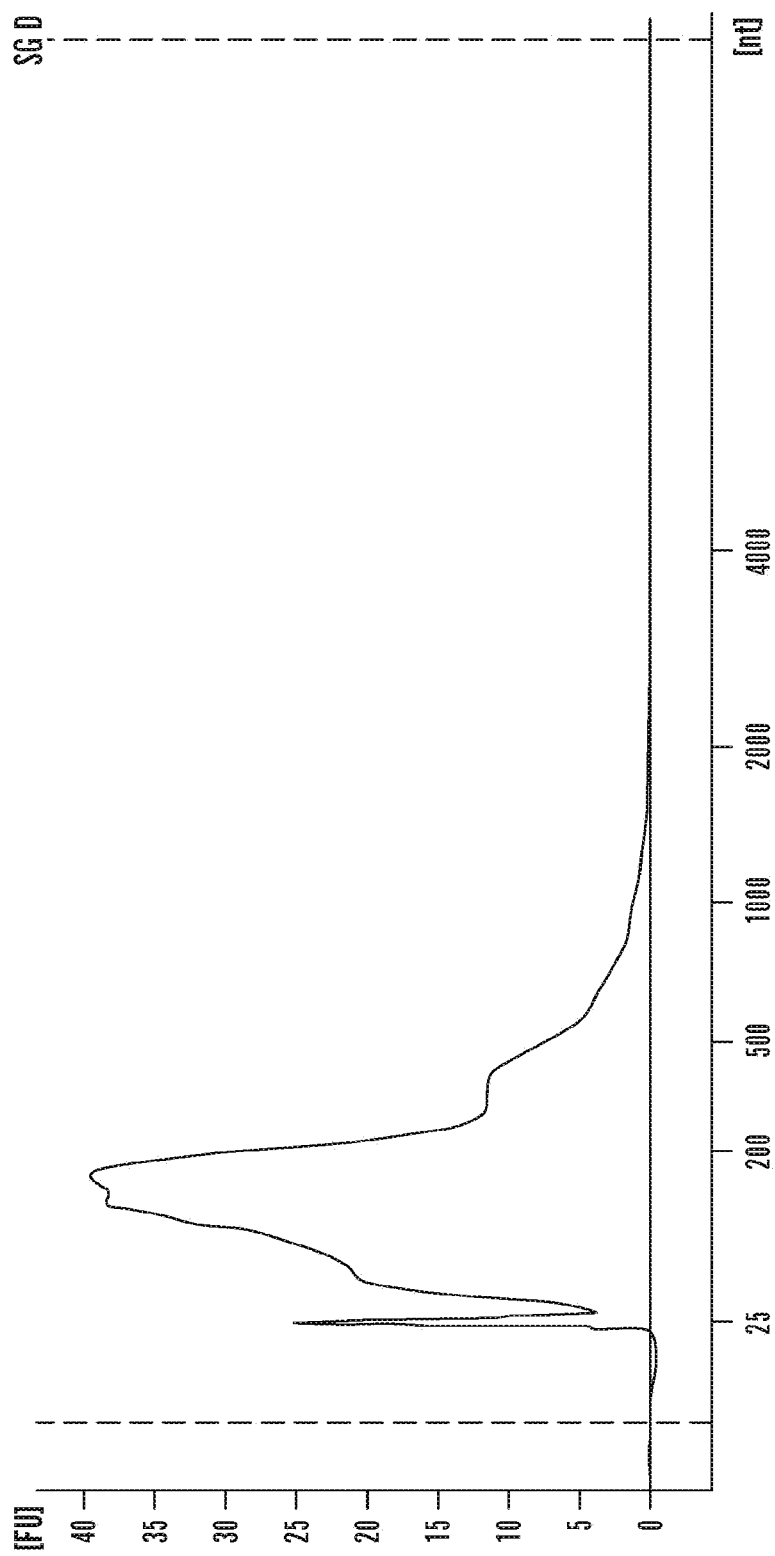
FIG. 1. Illustration of a bioanalyzer profile of RNAs extracted from serum exosomes. The nucleotide (nt) size is depicted on the x-axis, and the quantity is depicted on the y-axis as fluorescent units (FU).

A refers to plasma exosome DNA, no DNase treatment.
B refers to plasma exosome DNA, with DNase treatment on the outside of the exosome.
C refers to serum exosome DNA, no DNase treatment.
D refers to serum exosome DNA, with DNase treatment on the outside of the exosome.

DETAILED DESCRIPTION OF THE INVENTION

Microvesicles are shed by eukaryotic cells, or budded off of the plasma membrane, to the exterior of the cell. These membrane vesicles are heterogeneous in size with diameters ranging from about 10 nm to about 5000 nm. The small microvesicles (approximately 10 to 1000 nm, and more often approximately 30 to 200 nm in diameter) that are released by exocytosis of intracellular multivesicular bodies are referred to in the art as "exosomes." The methods and compositions described herein are equally applicable to microvesicles of all sizes; preferably 30 to 800 nm: and more preferably 30 to 200 nm.

In some of the literature, the term "exosome" also refers to protein complexes containing exoribonucleases which are involved in mRNA degradation and the processing of small nucleolar RNAs (snoRNAs), small nuclear RNAs (snRNAs) and ribosomal RNAs (rRNA) (Liu, et al. 2006; van Dijk, et al. 2007). Such protein complexes do not have membranes and are not "microvesicles" or "exosomes" as those terms are used herein.

Certain aspects of the present invention are based on the finding that the nucleic acids found within microvesicles can be used as valuable biomarkers for tumor diagnosis, characterization and prognosis by providing a genetic biomarker or profile. The nucleic acids within microvesicles can also be used to monitor tumor progression over time by analyzing if other mutations are acquired during tumor progression as well as if the levels of certain mutations are becoming increased or decreased over time or over a course of treatment (Skog et al., WO 2009/100029).

Certain aspects of the present invention are based on the finding that the ability to analyze nucleic acids from microvesicles provides a non-invasive and sensitive method for detecting genetic aberrations. This ability to detect genetic aberrations provides for the ability to detect, diagnose, monitor, treat, or evaluate a disease or other medical condition, by analyzing nucleic acid content from microvesicles. Moreover, nucleic acids from microvesicles may be isolated and analyzed periodically as a means to detect changes in nucleic acids. Such analyses can provide valuable information regarding the state of a disease or other medical condition, at the particular point in time that the microvesicles were obtained from the subject. This information may be used to assist in the therapeutic evaluation and decision-making process for a subject having a disease or other medical condition. For example, the presence or absence of one or more mutations in a particular gene may indicate the susceptibility to, presence of, or progression of a disease or other medical condition in a subject, or may indicate the likelihood that a particular therapeutic treatment will be efficacious. In particular, the KRAS mutation status is predictive of response to therapy with drugs such as cetuximab and panitumumab (also known as Erbitux and Vectibix) (anti-EGFR inhibitors) in colorectal cancer Certain aspects of the present invention are based on another finding that most of the extracellular RNAs in bodily fluid of a subject are contained within microvesicles and thus protected from degradation by ribonucleases. More than 90% of extracellular RNA in total serum can be recovered in microvesicles (Skog et al., WO 2009/100029).

In general terms, the present invention relates to methods for diagnosing, prognosing, monitoring, and treating a disease or other medical condition in a subject comprising the steps of, isolating a microvesicle fraction (or obtaining a microvesicle preparation) from a bodily fluid of a subject, and analyzing one or more nucleic acids contained within the microvesicles. The nucleic acids are analyzed qualitatively and/or quantitatively, and the results are compared to results expected or obtained for one or more other subjects who have or do not have the disease or other medical condition. The presence of a difference in microvesicular nucleic acid content of the subject, as compared to a reference (e.g., microvesicular nucleic acid content of one or more other individuals, or prior analyses of the microvesicular nucleic content of the same individual) can indicate the presence or absence of a disease or other medical condition, the progression of said disease or other medical condition (e.g., changes of tumor size and tumor malignancy), the susceptibility to a disease or other medical condition, or the efficacy of a drug or other therapeutic treatment for a particular subject.

The compositions, methods and techniques described herein provide the following advantages: 1) the opportunity to selectively analyze disease- or tumor-specific nucleic acids, which may be realized by isolating disease- or tumor-specific microvesicles apart from other microvesicles within the fluid sample; 2) significantly higher yield of nucleic acid species with higher sequence integrity as compared to the yield/integrity obtained by extracting nucleic acids directly from the fluid sample; 3) scalability, e.g. to detect nucleic acids expressed at low levels, the sensitivity can be increased by isolating more microvesicles from a larger volume of serum; 4) purer nucleic acids in that protein and lipids, debris from dead cells, and other potential contaminants and PCR inhibitors are excluded from the microvesicle preparation before the nucleic acid extraction step; and 5) more choices in nucleic acid extraction methods as microvesicle preparations are of much smaller volume than that of the starting serum, making it possible to extract nucleic acids from these microvesicle preparations using small volume column filters.

The microvesicles are preferably isolated from a bodily fluid from a subject. As used herein, a "bodily fluid" refers to a sample of fluid isolated from anywhere in the body of the subject, preferably a peripheral location, including but not limited to, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof.

The term "subject" is intended to include all animals shown to or expected to have microvesicles. In particular embodiments, the subject is a mammal, a human or nonhuman primate, a dog, a cat, a horse, a cow, other farm animals, or a rodent (e.g. mice, rats, guinea pig, etc.). The term "subject" and "individual" are used interchangeably herein.

Methods of isolating microvesicles from a biological sample are known in the art. For example, a method of differential centrifugation is described in a paper by Raposo, et al. (Raposo, et al. 1996), and similar methods are detailed in the Examples section herein. Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in (Taylor and Gercel-Taylor 2008). A method of nanomembrane ultrafiltration concentrator is described in (Cheruvanky, et al. 2007). Preferably, microvesicles can be identified and isolated from bodily fluid of a subject by a recently developed microchip technology that uses a unique microfluidic platform to efficiently and selectively separate tumor derived microvesicles. This technology, as described in a paper by Nagrath, et al. (Nagrath, et al. 2007), can be adapted to identify and separate microvesicles using similar principles of capture and separation as taught in the paper. Further, methods of isolating microvesicles from urine samples are described in a paper by Miranda, et al. (Miranda, et al. 2010) and in Russo, et al., PCT/US10/042365, filed Jul. 16, 2010 (expected to publish in 2011). Each of the foregoing references is incorporated by reference herein for its teaching of these methods.

In one embodiment, the microvesicles isolated from a bodily fluid are enriched for those originating from a specific cell type, for example, lung, pancreas, stomach, intestine, bladder, kidney, ovary, testis, skin, colorectal, breast, prostate, brain, esophagus, liver, placenta, fetus cells. Because the microvesicles often carry surface molecules such as antigens from their donor cells, surface molecules may be used to identify, isolate and/or enrich for microvesicles from a specific donor cell type (Al-Nedawi, et al. 2008: Taylor and Gercel-Taylor 2008). In this way, microvesicles originating from distinct cell populations can be analyzed for their nucleic acid content. For example, tumor (malignant and non-malignant) microvesicles carry tumor-associated surface antigens and may be detected, isolated and/or enriched via these specific tumor-associated surface antigens. In one example, the surface antigen is epithelial-cell-adhesion-molecule (EpCAM), which is specific to microvesicles from carcinomas of lung, colorectal, breast, prostate, head and neck, and hepatic origin, but not of hematological cell origin (Balzar, et al. 1999; Went, et al. 2004). In another example, the surface antigen is CD24, which is a glycoprotein specific to urine microvesicles (Keller, et al. 2007). In yet another example, the surface antigen is selected from a group of molecules CD70, carcinoembryonic antigen (CEA), EGFR, EGFRvIII and other variants, Fas ligand, TRAIL, tranferrin receptor, p38.5, p97 and HSP72. Additionally, tumor specific microvesicles may be characterized by the lack of surface markers, such as CD80 and CD86.

The isolation of microvesicles from specific cell types can be accomplished, for example, by using antibodies, aptamers, aptamer analogs or molecularly imprinted polymers specific for a desired surface antigen. In one embodiment, the surface antigen is specific for a cancer type. In another embodiment, the surface antigen is specific for a cell type which is not necessarily cancerous. One example of a method of microvesicle separation based on cell surface antigen is provided in U.S. Pat. No. 7,198,923. As described in, e.g., U.S. Pat. Nos. 5,840,867 and 5,582,981, WO 2003/050290 and a publication by Johnson, et al. (Johnson, et al. 2008), aptamers and their analogs specifically bind surface molecules and can be used as a separation tool for retrieving cell type-specific microvesicles. Molecularly imprinted polymers also specifically recognize surface molecules as described in, e.g., U.S. Pat. Nos. 6,525,154, 7,332,553 and 7,384,589 and a publication by Bossi, et al. (Bossi, et al. 2007) and are a tool for retrieving and isolating cell type-specific microvesicles. Each of the foregoing reference is incorporated herein for its teaching of these methods.

It may be beneficial or otherwise desirable to extract the nucleic acid from the exosomes prior to the analysis. Nucleic acid molecules can be isolated from a microvesicle using any number of procedures, which are well-known in the art, the particular extraction procedure chosen being appropriate for the particular biological sample. For example, methods for extracting nucleic acids from urinary microvesicles are described in Miranda, et al. (Miranda, et al. 2010) and in Russo, et al., PCT/US10/042365, filed Jul. 16, 2010 (expected to publish in 2011), each of which is incorporated herein for its teaching of these methods. In some instances, with some techniques, it may also be possible to analyze the nucleic acid without extraction from the microvesicle.

In one embodiment, the extracted nucleic acids, including DNA and/or RNA, are analyzed directly without an amplification step. Direct analysis may be performed with different methods including, but not limited to, nanostring technology. NanoString technology enables identification and quantification of individual target molecules in a biological sample by attaching a color coded fluorescent reporter to each target molecule. This approach is similar to the concept of measuring inventory by scanning barcodes. Reporters can be made with hundreds or even thousands of different codes allowing for highly multiplexed analysis. The technology is described in a publication by Geiss, et al. (Geiss, et al. 2008) and is incorporated herein by reference for this teaching.

In another embodiment, it may be beneficial or otherwise desirable to amplify the nucleic acid of the microvesicle prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a profile as described below.

In one embodiment, the extracted nucleic acid is DNA. In another embodiment, the extracted nucleic acid is RNA. RNAs are preferably reverse-transcribed into complementary DNAs. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self sustained sequence replication and its variants (Guatelli, et al. 1990), transcriptional amplification system and its variants (Kwoh, et al. 1989), Qb Replicase and its variants (Miele, et al. 1983), cold-PCR (Li, et al. 2008) or any other nucleic acid amplification methods, followed by the detection of the amplified molecules using techniques known to those of skill in the art. Especially useful are those detection schemes designed for the detection of nucleic acid molecules if such molecules are present in very low numbers. The foregoing references are incorporated herein for their teachings of these methods.

The analysis of nucleic acids present in the microvesicles is quantitative and/or qualitative. For quantitative analysis, the amounts (expression levels), either relative or absolute, of specific nucleic acids of interest within the microvesicles are measured with methods known in the art. For qualitative analysis, the species of specific nucleic acids of interest within the microvesicles, whether wild type or variants, are identified with methods known in the art.

"Genetic aberrations" is used herein to refer to the nucleic acid amounts as well as nucleic acid variants within the microvesicles. Specifically, genetic aberrations include, without limitation, over-expression of a gene (e.g., oncogenes) or a panel of genes, under-expression of a gene (e.g., tumor suppressor genes such as p53 or RB) or a panel of genes, alternative production of splice variants of a gene or a panel of genes, gene copy number variants (CNV) (e.g. DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splicing variants and/or changes of gene expression level.

The determination of such genetic aberrations can be performed by a variety of techniques known to the skilled practitioner. For example, expression levels of nucleic acids, alternative splicing variants, chromosome rearrangement and gene copy numbers can be determined by microarray analysis (U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers, et al. 2006). Nucleic acid modifications can be assayed by methods described in, e.g., U.S. Pat. No. 7,186,512 and patent publication WO 2003/023065. Particularly, methylation profiles may be determined by Illumina DNA Methylation OMA003 Cancer Panel. SNPs and mutations can be detected by hybridization with allele-specific probes, enzymatic mutation detection, chemical cleavage of mismatched heteroduplex (Cotton, et al. 1988), ribonuclease cleavage of mismatched bases (Myers, et al. 1985), mass spectrometry (U.S. Pat. Nos. 6,994,960, 7,074,563, and 7,198,893), nucleic acid sequencing, single strand conformation polymorphism (SSCP) (Orita, et al. 1989), denaturing gradient gel electrophoresis (DGGE) (Fischer and Lerman 1979a; Fischer and Lerman 1979b), temperature gradient gel electrophoresis (TGGE) (Fischer and Lerman 1979a; Fischer and Lerman 1979b), restriction fragment length polymorphisms (RFLP) (Kan and Dozy 1978a; Kan and Dozy 1978b), oligonucleotide ligation assay (OLA), allele-specific PCR (ASPCR) (U.S. Pat. No. 5,639,611), ligation chain reaction (LCR) and its variants (Landegren, et al. 1988; Nakazawa, et al. 1994; Abravaya, et al. 1995), flow-cytometric heteroduplex analysis (WO/2006/113590) and combinations or modifications of any of the foregoing. In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated. The forgoing references are incorporated herein for their teachings of these methods.

The published literature describes a variety of genetic aberrations that have been identified to occur and/or contribute to the initial generation or progression of cancer. Examples of genes which are commonly under expressed, or over expressed in brain tumors are reviewed in (Furnari, et al. 2007), and this subject matter is incorporated herein by reference. With respect to the development of brain tumors, RB and p53 are often down-regulated to otherwise decrease their tumor suppressive activity. Therefore, in these embodiments, the presence or absence of an increase or decrease in the nucleic acid expression level of a gene(s) and/or a microRNA(s) whose disregulated expression level is specific to a type of cancer can be used to indicate the presence or absence of the type of cancer in the subject.

Likewise, nucleic acid variants, e.g., DNA or RNA modifications, single nucleotide polymorphisms (SNPs) and mutations (e.g., missense, nonsense, insertions, deletions, duplications) may also be analyzed within microvesicles from bodily fluid of a subject, including pregnant females where microvesicles derived from the fetus may be in serum as well as amniotic fluid.

In addition, more genetic aberrations associated with cancers have been identified recently in a few ongoing research projects. For example, the Cancer Genome Atlas (TCGA) program is exploring a spectrum of genomic changes involved in human cancers. The results of this project and other similar research efforts are published and incorporated herein by reference (Wood, et al. 2007; Jones, et al. 2008; McLendon, et al. 2008; Parsons, et al. 2008). Specifically, these research projects have identified genetic aberrations, such as mutations (e.g., missense, nonsense, insertions, deletions and duplications), gene expression level variations (mRNA or microRNA), copy number variations and nucleic acid modification (e.g. methylation), in human glioblastoma, pancreatic cancer, breast cancer and/or colorectal cancer. Any genetic aberrations associated with cancer are targets that may be selected for use in diagnosing and/or monitoring cancer by the methods described herein.

The RAS family of oncogenes is commonly mutated in cancer. The Ras family consists of Hras, Kras, and Nras genes, all of which encode for GTP-binding proteins that act to transmit signals from receptor tyrosine kinases to downstream modulators of cell growth. In roughly 20% of all human cancers, an activating mutation in a Ras gene is found. In 85% of those cases, the mutated Ras gene is the Kras gene. Additionally, Kras mutations are found in roughly 50% of all colorectal cancers (Jancik et al. 2010). During tumorigenesis, aberrant Ras signaling can lead to uncontrolled cell proliferation and resistance to apoptosis. Moreover, Ras has been shown to play an important role in the expression of matrix metalloproteinases, as well as other processes that promote tumor invasion and metastasis.

The ability to detect genetic aberrations in microvesicles of a subject provides a useful model for practicing companion diagnostics. Based on analyses of nucleic acids from the microvesicles of a subject having a disease or other medical condition, therapeutic treatment may be tailored for that subject. For example, a companion diagnostic test kit may be developed to test for one or more mutations in the Kras gene. Based on the presence or absence of such mutations, a particular therapeutic treatment may or may not be recommended.

The Kras protein regulates two signaling pathways: (1) PI 3-kinase/phosphatase and tensin homolog (PTEN)/AKT; and (2) RAF/MEK/ERK. These pathways are popular targets for anti-cancer therapies, including drugs which target Epidermal Growth Factor Receptor (EGFR), upstream from Kras. When bound to its ligand, EGFR initiates tyrosine kinase activity, activating Kras, and the signaling pathways (Quest Diagnostics, KRAS Mutation Analysis, Reference Materials.

Existing therapies that target EGFR are used to treat various cancers, including colorectal cancer and non-small-cell cancer. These therapies employ either: (a) monoclonal antibodies, such as cetuximab or panitumumab, that abrogate ligand binding and, thus, EGFR activation; or (b) tyrosine kinease inhibitors, such as erlotinib, that prevent activation of the signaling pathways. However, such therapies are rendered ineffective when the defect in the signaling pathway occurs downstream of these targets (Quest Diagnostics, KRAS Mutation Analysis, Reference Materials.

Kras mutations in cancers are frequently found in codons 12, 13, and 61. Mutations in codons 12 and 13 of Kras have been associated with unresponsiveness to EGFR-targeted therapies in both colorectal cancer and non-small-cell cancer. Accordingly, cancer patients bearing mutations in codons 12 and 13 should not receive treatment that targets the EGFR, and should be treated with alternative therapies with different targets (Quest Diagnostics, KRAS Mutation Analysis, Reference Materials.

Seven common somatic mutations of the Kras gene are depicted in Table 1:

TABLE 1

KRAS Mutations

| Mutation (Codon Number) | Base Change |
|---|---|
| Gly12Ala | GGT > GCT |
| Gly12Asp | GGT > GAT |
| Gly12Arg | GGT > CGT |
| Gly12Cys | GGT > TGT |
| Gly12Ser | GGT > AGT |
| Gly12Val | GGT > GTT |
| Gly13Asp | GGC > GAC |

Detection of one or more nucleotide variants can be accomplished by performing a nucleotide variant screen on the nucleic acids within the microvesicles. Such a screen can be as wide or narrow as determined necessary or desirable by the skilled practitioner. It can be a wide screen (set up to detect all possible nucleotide variants in genes known to be associated with one or more cancers or disease states). Where one specific cancer or disease is suspected or known to exist, the screen can be specific to that cancer or disease. One example is a brain tumor/brain cancer screen (e.g., set up to detect all possible nucleotide variants in genes associated with various clinically distinct subtypes of brain cancer or known drug-resistant or drug-sensitive mutations of that cancer).

In one embodiment, the analysis is of a profile of the amounts (levels) of specific nucleic acids present in the microvesicle, herein referred to as a "quantitative nucleic acid profile" of the microvesicles. In another embodiment, the analysis is of a profile of the species of specific nucleic acids present in the microvesicles (both wild type as well as variants), herein referred to as a "nucleic acid species profile." A term used herein to refer to a combination of these types of profiles is "genetic profile" which refers to the determination of the presence or absence of nucleotide species, variants and also increases or decreases in nucleic acid levels.

Once generated, these genetic profiles of the microvesicles are compared to those expected in, or otherwise derived from a healthy normal individual. A profile can be a genome wide profile (set up to detect all possible expressed genes or DNA sequences). It can be narrower as well, such as a cancer wide profile (set up to detect all possible genes or nucleic acids derived therefrom, or known to be associated with one or more cancers). Where one specific cancer is suspected or known to exist, the profile can be specific to that cancer (e.g., set up to detect all possible genes or nucleic acids derived therefrom, associated with various clinically distinct subtypes of that cancer or known drug-resistant or sensitive mutations of that cancer).

Which nucleic acids are to be amplified and/or analyzed can be selected by the skilled practitioner. The entire nucleic acid content of the exosomes or only a subset of specific nucleic acids which are likely or suspected of being influenced by the presence of a disease or other medical condition such as cancer, can be amplified and/or analyzed. The identification of a nucleic acid aberration(s) in the analyzed microvesicle nucleic acid can be used to diagnose the subject for the presence of a disease such as cancer, hereditary diseases or viral infection with which that aberration(s) is associated. For instance, analysis for the presence or absence of one or more nucleic acid variants of a gene specific to a cancer (e.g. the Kras mutation) can indicate the cancer's presence in the individual.

In one embodiment, mutations of a gene which is associated with a disease such as cancer (e.g. via nucleotide variants, over-expression or under-expression) are detected by analysis of nucleic acids in microvesicles, which nucleic acids are derived from the genome itself in the cell of origin or exogenous genes introduced through viruses. The nucleic acid sequences may be complete or partial, as both are expected to yield useful information in diagnosis and prognosis of a disease. The sequences may be sense or anti-sense to the actual gene or transcribed sequences. The skilled practitioner will be able to devise detection methods for a nucleotide variance from either the sense or anti-sense nucleic acids which may be present in a microvesicle. Many such methods involve the use of probes which are specific for the nucleotide sequences which directly flank, or contain the nucleotide variances. Such probes can be designed by the skilled practitioner given the knowledge of the gene sequences and the location of the nucleic acid variants within the gene. Such probes can be used to isolate, amplify, and/or actually hybridize to detect the nucleic acid variants, as described in the art and herein.

Determining the presence or absence of a particular nucleotide variant or plurality of variants in the nucleic acid within microvesicles from a subject can be performed in a variety of ways. A variety of methods are available for such analysis, including, but not limited to, PCR, hybridization with allele-specific probes, enzymatic mutation detection, chemical cleavage of mismatches, mass spectrometry or DNA sequencing, including minisequencing. In particular embodiments, hybridization with allele specific probes can be conducted in two formats: 1) allele specific oligonucleotides bound to a solid phase (glass, silicon, nylon membranes) and the labeled sample in solution, as in many DNA chip applications, or 2) bound sample (often cloned DNA or PCR amplified DNA) and labeled oligonucleotides in solution (either allele specific or short so as to allow sequencing by hybridization). Diagnostic tests may involve a panel of variances, often on a solid support, which enables the simultaneous determination of more than one variance. In another embodiment, determining the presence of at least one nucleic acid variance in the microvesicle nucleic acid entails a haplotyping test. Methods of determining haplotypes are known to those of skill in the art, as for example, in WO 00/04194.

In one embodiment, the determination of the presence or absence of a nucleic acid variant(s) involves determining the sequence of the variant site or sites (the exact location within the sequence where the nucleic acid variation from the norm occurs) by methods such as polymerase chain reaction (PCR), chain terminating DNA sequencing (U.S. Pat. No. 5,547,859), minisequencing (Fiorentino, et al. 2003), oligonucleotide hybridization, pyrosequencing, Illumina genome analyzer, deep sequencing, mass spectrometry or other nucleic acid sequence detection methods. Methods for detecting nucleic acid variants are well known in the art and disclosed in WO 00/04194, incorporated herein by reference. In an exemplary method, the diagnostic test comprises amplifying a segment of DNA or RNA (generally after converting the RNA to complementary DNA) spanning one or more known variants in the desired gene sequence. This amplified segment is then sequenced and/or subjected to electrophoresis in order to identify nucleotide variants in the amplified segment.

In one embodiment, the invention provides a method of screening for nucleotide variants in the nucleic acid of microvesicles isolated as described herein. This can be achieved, for example, by PCR or, alternatively, in a ligation chain reaction (LCR) (Landegren, et al. 1988: Nakazawa, et al. 1994; Abravaya, et al. 1995). LCR can be particularly useful for detecting point mutations in a gene of interest (Abravaya, et al. 1995). The LCR method comprises the steps of designing degenerate primers for amplifying the target sequence, the primers corresponding to one or more conserved regions of the nucleic acid corresponding to the gene of interest, amplifying PCR products with the primers using, as a template, a nucleic acid obtained from a microvesicle, and analyzing the PCR products. Comparison of the PCR products of the microvesicle nucleic acid to a control sample (either having the nucleotide variant or not) indicates variants in the microvesicle nucleic acid. The change can be either an absence or presence of a nucleotide variant in the microvesicle nucleic acid, depending upon the control.

In one embodiment, the invention provides a method of screening for nucleotide variants of the Kras gene isolated from microvesicles. In one embodiment, the detection of mutations in the Kras gene is performed by a real-time PCR assay using a KRAS PCR Kit (Qiagen®). While the KRAS PCR Kit is intended to be used with genomic DNA samples, it may also be employed for use with other nucleic acid samples that are not derived from genomic DNA, provided the KRAS PCR Kit is modified. For example, in another embodiment, the KRAS PCR Kit is modified to quantitatively detect Kras mutants from RNA samples. Isolated RNA is reverse transcribed via Reverse Transcriptase (RT) into complementary DNA (cDNA). In order to remove the impurities from the RT reaction, the cDNA sample is purified using standard techniques known in the art for purifying DNA, including, e.g., by ethanol precipitation and via purification columns. Alternatively, the cDNA may be diluted. Once it is substantially free from the impurities of the RT reaction, either by purification or dilution, the cDNA sample is subject to the amplification steps of the KRAS PCR Kit. Because of this modification, i.e., the added step of purifying the cDNA template prior to amplification, the KRAS PCR Kit may be employed to detect, quantify, and analyze RNA samples.

Many methods of diagnosis performed on a tumor biopsy sample can be performed with microvesicles since tumor cells are known to shed microvesicles into bodily fluid and the genetic aberrations within these microvesicles reflect those within tumor cells as demonstrated herein. Furthermore, methods of diagnosis using microvesicles have characteristics that are absent in methods of diagnosis performed directly on a tumor biopsy sample. For example, one particular advantage of the analysis of microvesicular nucleic acids, as opposed to other forms of sampling of tumor/cancer nucleic acid, is the availability for analysis of tumor/cancer nucleic acids derived from all foci of a tumor or genetically heterogeneous tumors present in an individual. Biopsy samples are limited in that they provide information only about the specific focus of the tumor from which the biopsy is obtained. Different tumorous/cancerous foci found within the body, or even within a single tumor often have different genetic profiles and are not analyzed in a standard biopsy. However, analysis of the microvesicular nucleic acids from an individual presumably provides a sampling of all foci within an individual. This provides valuable information with respect to recommended treatments, treatment effectiveness, disease prognosis, and analysis of disease recurrence, which cannot be provided by a simple biopsy.

In one embodiment, the microvesicle fraction from a bodily fluid of a subject is pre-treated with DNase to eliminate or substantially eliminate all of any DNA located on the surface of the microvesicles or outside of the microvesicles. Without DNAse pre-treatment, short DNA fragments on the outside of microvesicles may remain and co-isolate with nucleic acids extracted from inside the microvesicles. Thus, elimination of all or substantially all of any DNA associated with the outside or surface of microvesicles by pre-treatment of the microvesicles with DNase, has the ability to enrich for nucleic acid from within the microvesicles.

Identification of genetic aberrations associated with specific diseases and/or medical conditions by the methods described herein can also be used for prognosis and treatment decisions of an individual diagnosed with a disease or other medical condition such as cancer. Identification of the genetic basis of a disease and/or medical condition provides useful information guiding the treatment of the disease and/or medical condition. For example, many forms of chemotherapy have been shown to be more effective on cancers with specific genetic abnormalities/aberrations. One example is the effectiveness of EGFR-targeting treatments with medicines, such as the kinase inhibitors gefitinib and erlotinib. Such treatments have been shown to be more effective on cancer cells whose EGFR gene harbors specific nucleotide mutations in the kinase domain of the EGFR protein (U.S. Patent publication 20060147959). In other words, the presence of at least one of the identified nucleotide variants in the kinase domain of EGFR nucleic acid message indicates that a patient will likely benefit from treatment with the EGFR-targeting compound gefitinib or erlotinib. Such nucleotide variants can be identified in nucleic acids present in microvesicles by the methods described herein.

Genetic aberrations in other genes have also been found to influence the effectiveness of treatments. As disclosed in the publication by Furnari et al. (Furnari, et al. 2007), mutations in a variety of genes affect the effectiveness of specific medicines used in chemotherapy for treating brain tumors. The identification of these genetic aberrations in the nucleic acids within microvesicles has the potential to guide the selection of proper treatment plans.

Other aspects of the present invention relate to a method for monitoring disease (e.g. cancer) progression in a subject, and also to a method for monitoring disease recurrence in an individual. These methods comprise the steps of isolating microvesicles from a bodily fluid of an individual, as discussed herein, and analyzing nucleic acid within the microvesicles as discussed herein (e.g. to create a genetic profile of the microvesicles). The presence/absence of a certain genetic aberration/profile is used to indicate the presence/absence of the disease (e.g. cancer) in the subject as discussed herein. The process is performed periodically over time, and the results reviewed, to monitor the progression or regression of the disease, or to determine recurrence of the disease. Put another way, a change in the genetic profile indicates a change in the disease state in the subject. The period of time to elapse between sampling of microvesicles from the subject, for performance of the isolation and analysis of the microvesicle, will depend upon the circumstances of the subject, and is to be determined by the skilled practitioner. Such a method would prove extremely beneficial when analyzing a nucleic acid from a gene that is associated with the therapy undergone by the subject. For example, a gene which is targeted by the therapy can be monitored for the development of mutations which make it resistant to the therapy, upon which time the therapy can be modified accordingly. The monitored gene may also be one which indicates specific responsiveness to a specific therapy.

Aspects of the present invention also relate to the fact that a variety of non-cancer diseases and/or medical conditions also have genetic links and/or causes, and such diseases and/or medical conditions can likewise be diagnosed and/or monitored by the methods described herein. Many such diseases are metabolic, infectious or degenerative in nature. One such disease is diabetes (e.g. diabetes insipidus) in which the vasopressin type 2 receptor (V2R) is modified. Another such disease is kidney fibrosis in which the genetic profiles for the genes of collagens, fibronectin and TGF-☐ are changed. Changes in the genetic profile due to substance abuse (e.g. a steroid or drug use), viral and/or bacterial infection, and hereditary disease states can likewise be detected by the methods described herein.

Diseases or other medical conditions for which the inventions described herein are applicable include, but are not limited to, nephropathy, diabetes insipidus, diabetes mellitus, diabetes type I, diabetes H, renal disease glomerulonephritis, bacterial or viral glomerulonephritides, IgA nephropathy, Henoch-Schonlein Purpura, membranoproliferative glomerulonephritis, membranous nephropathy, Sjogren's syndrome, nephrotic syndrome minimal change disease, focal glomerulosclerosis and related disorders, acute renal failure, acute tubulointerstitial nephritis, pyelonephritis, GU tract inflammatory disease, Pre-clampsia, renal graft rejection, leprosy, reflux nephropathy, nephrolithiasis, genetic renal disease, medullary cystic, medullar sponge, polycystic kidney disease, autosomal dominant polycystic kidney disease, autosomal recessive polycystic kidney disease, tuberous sclerosis, von Hippel-Lindau disease, familial thinglomerular basement membrane disease, collagen III glomerulopathy, fibronectin glomerulopathy, Alport's syndrome, Fabry's disease, Nail-Patella Syndrome, congenital urologic anomalies, monoclonal gammopathies, multiple myeloma, amyloidosis and related disorders, febrile illness, familial Mediterranean fever, HIV infection-AIDS, inflammatory disease, systemic vasculitides, polyarteritis nodosa, Wegener's granulomatosis, polyarteritis, necrotizing and crecentic glomerulonephritis, polymyositis-dermatomyositis, pancreatitis, rheumatoid arthritis, systemic lupus erythematosus, gout, blood disorders, sickle cell disease, thrombotic thrombocytopenia purpura, Fanconi's syndrome, transplantation, acute kidney injury, irritable bowel syndrome, hemolytic-uremic syndrome, acute corticol necrosis, renal thromboembolism, trauma and surgery, extensive injury, burns, abdominal and vascular surgery, induction of anesthesia, side effect of use of drugs or drug abuse, circulatory disease myocardial infarction, cardiac failure, peripheral vascular disease, hypertension, coronary heart disease, non-atherosclerotic cardiovascular disease, atherosclerotic cardiovascular disease, skin disease, soriasis, systemic sclerosis, respiratory disease, COPD, obstructive sleep apnoea, hypoia at high altitude or endocrine disease, or acromegaly.

Selection of an individual from whom the microvesicles are isolated is performed by the skilled practitioner based upon analysis of one or more of a variety of factors. Such factors for consideration are whether the subject has a family history of a specific disease (e.g. a cancer), has a genetic predisposition for such a disease, has an increased risk for such a disease due to family history, genetic predisposition, other disease or physical symptoms which indicate a predisposition, or environmental reasons. Environmental reasons include lifestyle, exposure to agents which cause or contribute to the disease such as in the air, land, water or diet. In addition, having previously had the disease, being currently diagnosed with the disease prior to therapy or after therapy, being currently treated for the disease (undergoing therapy), being in remission or recovery from the disease, are other reasons to select an individual for performing the methods.

The methods described herein are optionally performed with the additional step of selecting a gene or nucleic acid for analysis, prior to the analysis step. This selection can be based on any predispositions of the subject, or any previous exposures or diagnosis, or therapeutic treatments experienced or concurrently undergone by the subject.

The cancer diagnosed, monitored or otherwise profiled, can be any kind of cancer. This includes, without limitation, epithelial cell cancers such as lung, ovarian, cervical, endometrial, breast, brain, colon and prostate cancers. Also included are gastrointestinal cancer, head and neck cancer, non-small cell lung cancer, cancer of the nervous system, kidney cancer, retina cancer, skin cancer, liver cancer, pancreatic cancer, genital-urinary cancer and bladder cancer, melanoma, and leukemia. In addition, the methods and compositions of the present invention are equally applicable to detection, diagnosis and prognosis of non-malignant tumors in an individual (e.g. neurofibromas, meningiomas and schwannomas).

The invention is further illustrated by the following examples, which should not be construed as further limiting.

EXAMPLES

Example 1: Method of Analyzing Kras Mutations Using Microvesicles Isolated from Serum and Plasma Samples Following proper protocols, serum and plasma samples from 12 colorectal cancer patients were obtained for the following analysis.

To isolate microvesicles, 0.6-2 milliliter serum was filtered through a 0.8 m filter to remove any cell contamination. Microvesicles were then pelleted by ultracentrifugation at 110,000×g for 70 minutes.

For the extraction of RNA from microvesicles, the pelleted microvesicles were incubated in an RNAse inhibitor solution for 20 minutes at room temperature. The RNase inhibitor can be obtained from various known vendors, e.g., SUPERase-In (Ambion Inc). Total RNA was then extracted from the RNAse-treated microvesicles using miRNeasy RNA extraction kit (Qiagen). Alternatively, various commercial RNA extraction kits such as the QIAamp RNA Blood Mini Kit from Qiagen, QIAamp viral RNA mini kit (Qiagen) and the MirVana RNA isolation kit from Ambion Inc. may be used according to the manufacturer's protocols. After treatment with DNAse according to the manufacturer's protocol, total RNA was eluted in 30 μl nuclease-free water.

The extracted RNAs were then analyzed using a Bioanalyzer RNA chip (Agilent Technologies) to confirm the quality of the RNA. See FIG. 1. The isolated RNAs were then analyzed by a quantitative PCR assay; namely, a modified Scorpion® Kras mutation detection method. The off-the-shelf KRAS Mutation Test Kit is intended for the detection of 7 somatic mutations in the KRAS oncogene. The kit is marketed and sold for use on DNA samples and will provide a qualitative assessment of mutation status. In our modified method, the isolated RNAs were first reverse-transcribed into cDNAs using a standard reverse transcription method, e.g., the Sensiscript RT kit (Qiagen). The RNA-reverse-transcribed cDNAs were then purified using micro-columns with filters capable of retaining molecules above 30 kDa or 20-40 nucleotides. The purified cDNAs were used in the Scorpion® Kras mutation detection PCR reactions.

Figure 2:
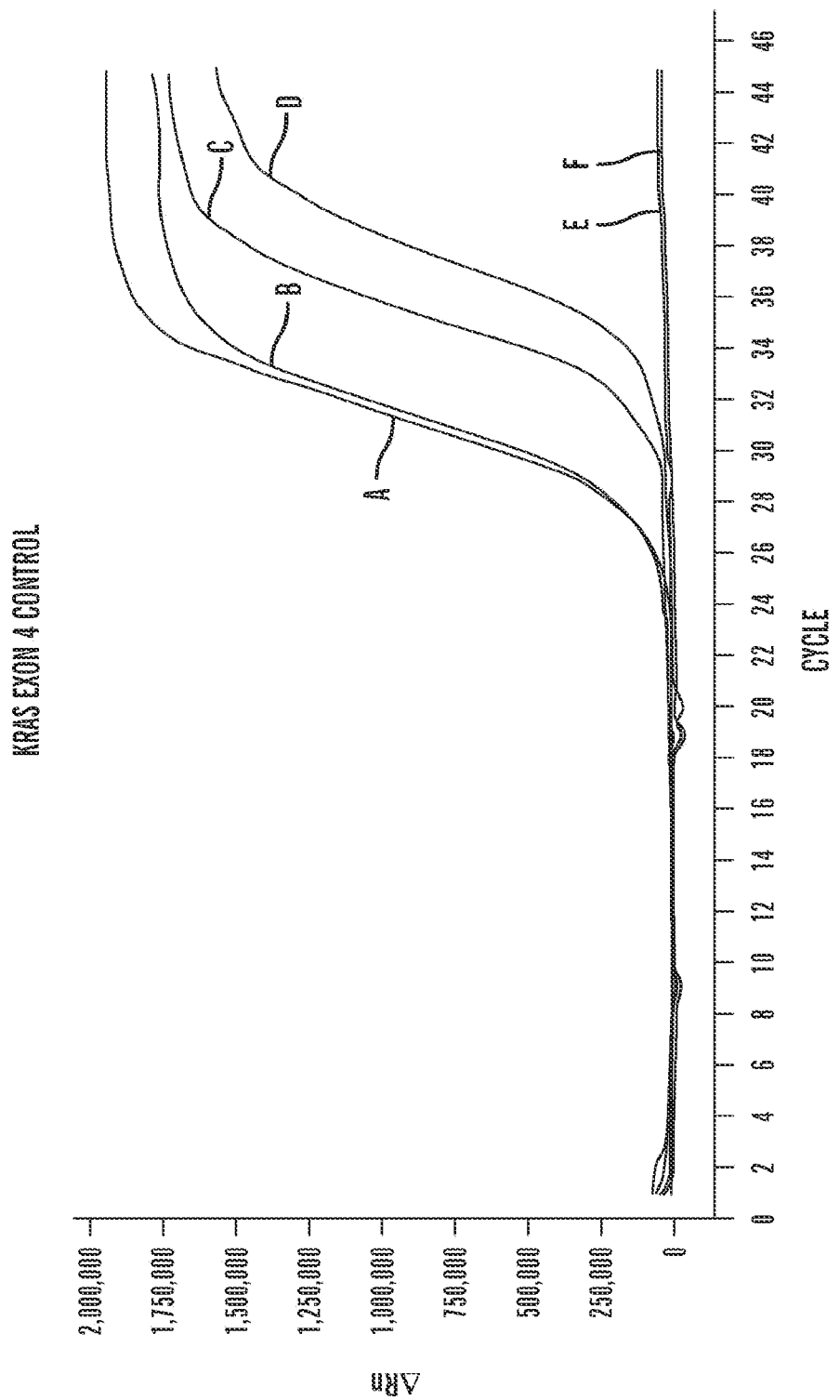
FIG. 2. Amplification plot illustrating the detection of Kras Exon 4 (a region that is not commonly mutated and therefore detects both mutated and wild type KRAS) using a modified Scorpion® mutation detection method. The PCR cycle number is shown on the x-axis, and the ARn (normalised fluorescence emission) versus cycle is shown on the y-axis. The Applied Biosystems 7500 Fast qPCR machine was used for the analysis (run in standard mode, as recommended by the Scorpion kit manufacturer, DxS of Manchester, England (now known as QIAGEN, Manchester, Ltd.; hereinafter referred to as "DxS")). The labels are as follows:
  A refers to a positive control (supplied by DxS).
  B refers to another positive control (supplied by DxS).
  C refers to serum exosome RNA from a colorectal cancer patient.
  D refers to plasma exosome RNA from a colorectal cancer patient.
  E refers to a negative control (no template control).
  F refers to a negative control (no template control).

As shown in FIG. 2, Kras Exon 4 can be readily detected when the cDNAs from serum and plasma exosomes were used. The number of cycles for the serum exosomes (C) was less than the number of cycles for the plasma exosomes (D), suggesting that serum RNA was more abundant than plasma RNA. As expected, the positive controls can be detected and the negative controls cannot.

Figure 3:
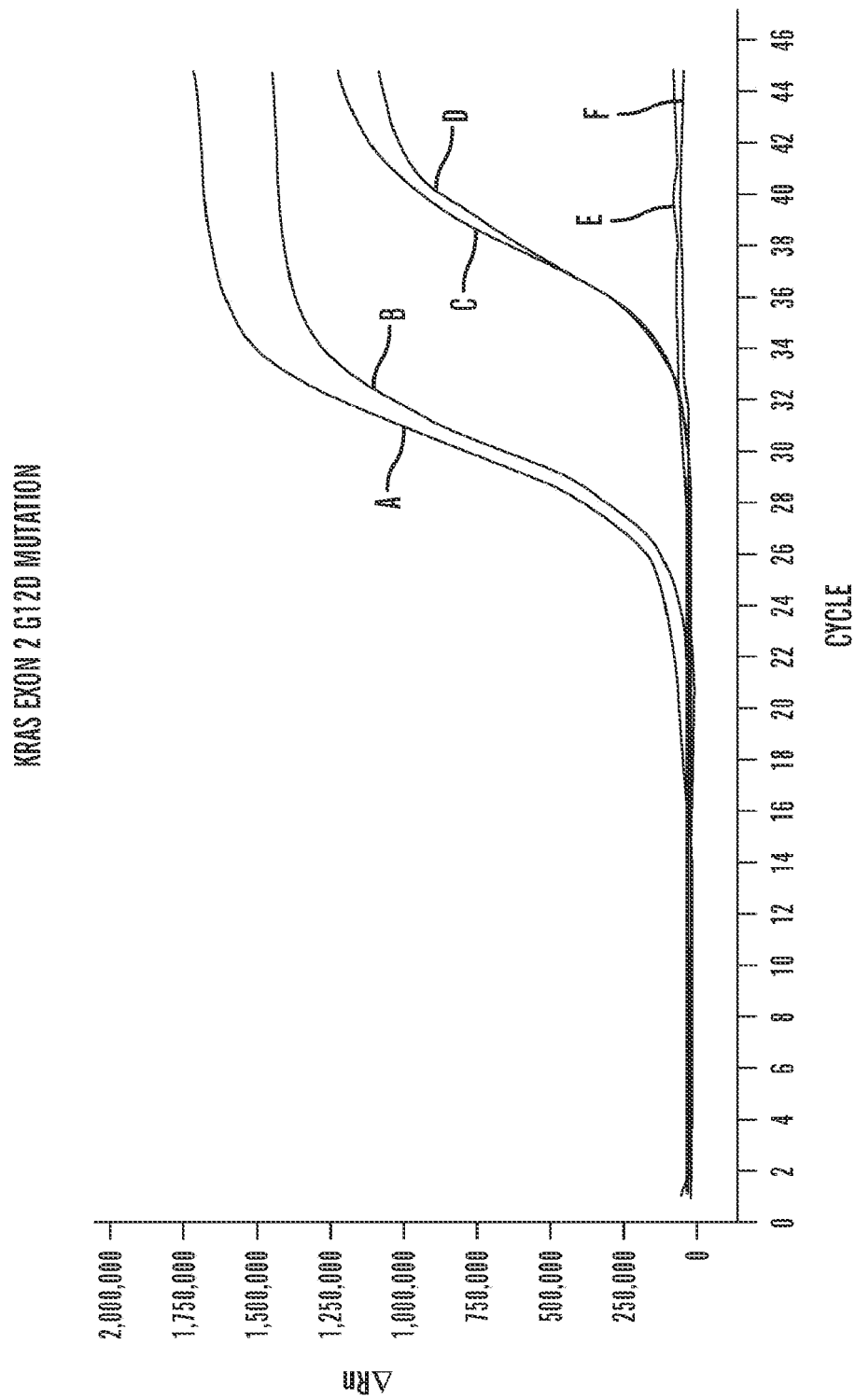
FIG. 3. Illustration of a result detecting Kras G12D mutation using a modified Scorpion® mutation detection method. The PCR cycle number is shown on the x-axis and the ΔRn (normalized fluorescence emission) versus cycle on the y-axis. The Applied Biosystems 7500 Fast qPCR machine was used for the analysis (run in standard mode, as recommended by the kit manufacturer, DxS). The labels are as follows:
  A refers to a positive control (mutation standard supplied by DxS).
  B refers to another positive control (mutation standard supplied by DxS).
  C refers to serum exosome RNA from the same patient designated with label C from FIG. 2, i.e., a colorectal cancer patient with confirmed KRAS GI2D mutation in the tumor.
  D refers to plasma exosome RNA from the same patient designated with label C from FIG. 2, i.e., a colorectal cancer patient with confirmed KRAS G12D mutation in the tumor.
  E refers to a negative control (no template control).
  F refers to a negative control (no template control).

In addition, as shown in FIG. 3, the Kras G12D mutation can be readily detected when the cDNAs from serum and plasma exosomes were used. The number of cycles for the serum exosomes (C) was similar to the number of cycles for the plasma exosomes (D), suggesting that serum exosomes RNA was as abundant as plasma exosome RNA. As expected, the positive controls can be detected and the negative controls cannot.

Overall, among the 12 patient serum samples, Kras mutations were detected in 3 true positive samples while Kras mutations were not detected in 2 true positive samples. However, Kras mutations were not detected in any of the true negative samples, demonstrating that the method disclosed here does not give false positives.

Figure 4A:
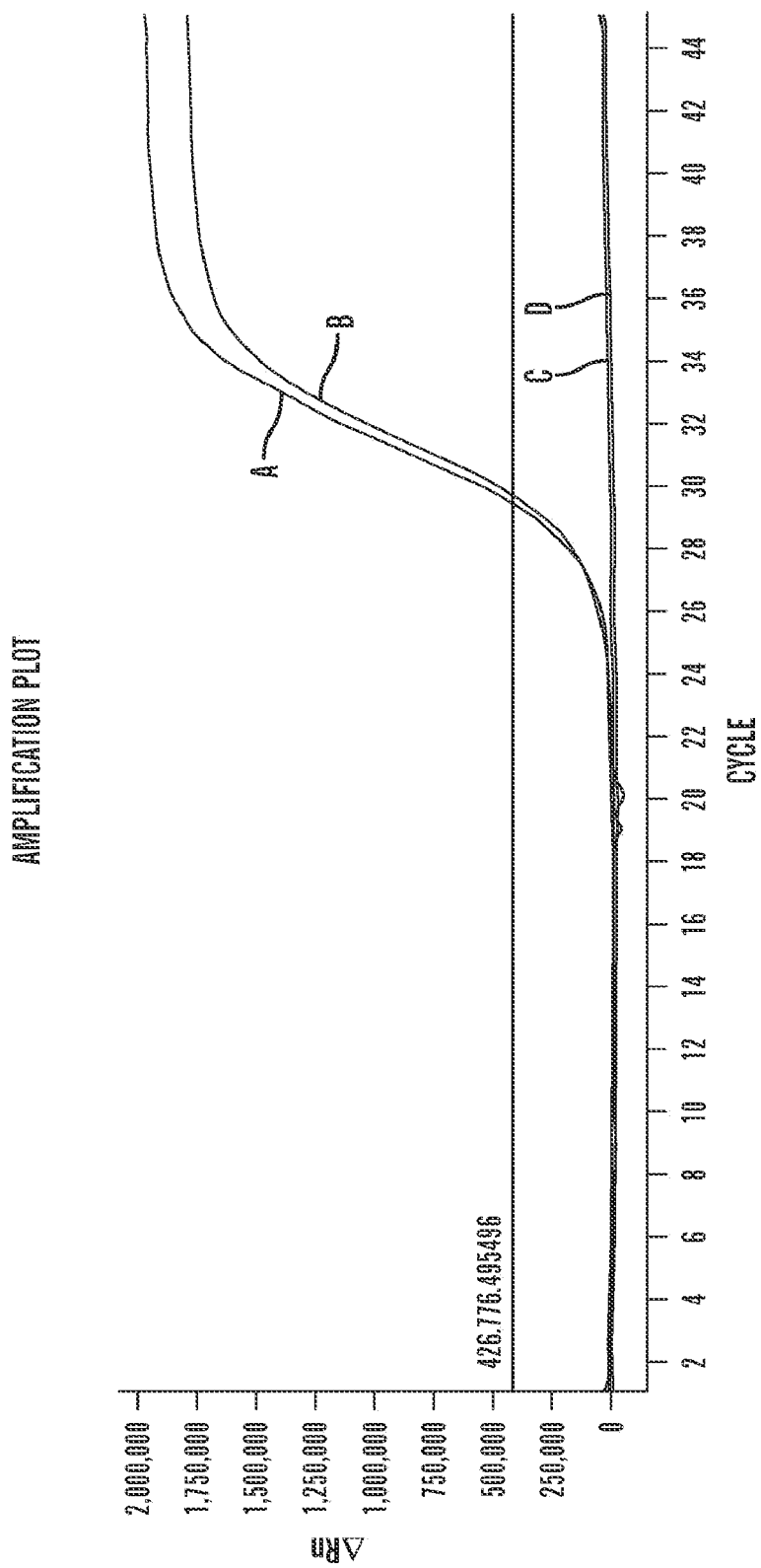
FIG. 4(a). Positive and negative control reaction for the detection of Kras Exon 4 (present in both mutated and wild type KRAS) using a modified Scorpion® mutation detection method. The PCR cycle number is shown on the x-axis and the ARn (normalized fluorescence emission) versus cycle on the y-axis. The Applied Biosystems 7500 Fast qPCR machine was used for the analysis (run in standard mode, as recommended by the kit manufacturer, DxS). The labels are as follows:
  A refers to a positive control (supplied by DxS).
  B refers to a positive control (supplied by DxS).
  C refers to a negative control (no template control).
  D refers to a negative control (no template control).
Figure 4B:
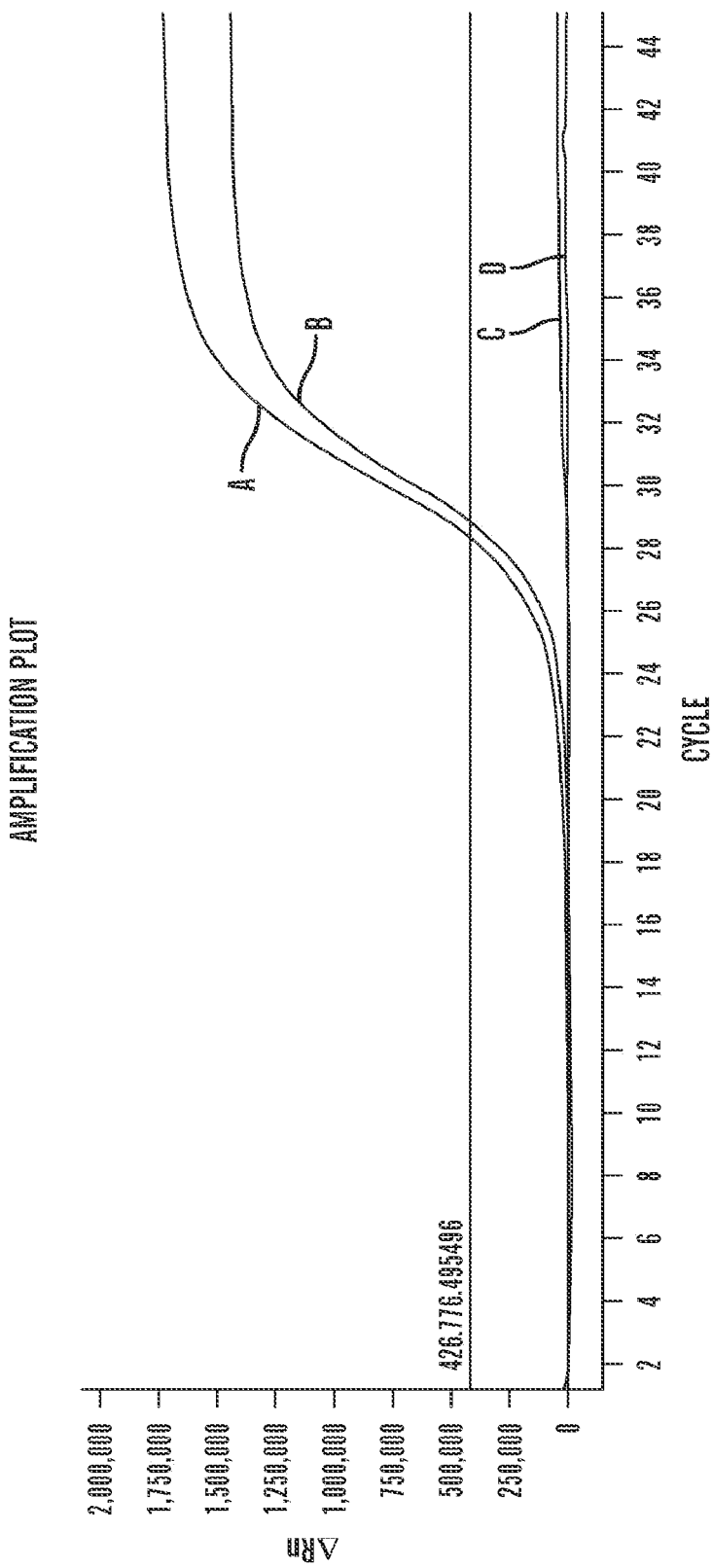
FIG. 4(b). Positive and negative control reaction for the detection of the Kras G12A mutation using a modified Scorpion® mutation detection method. The PCR cycle number is shown on the x-axis and the ARn (normalized fluorescence emission) versus cycle on the y-axis. The Applied Biosystems 7500 Fast qPCR machine was used for the analysis (run in standard mode, as recommended by the kit manufacturer, DxS). The labels are as follows:
  A refers to a positive control (mutation standard supplied by DxS).
  B refers to a positive control (mutation standard supplied by DxS).
  C refers to a negative control (no template control).
  D refers to a negative control (no template control).

Example 2: Positive and Negative Control Reactions for the Detection of Kras Exon 4 and Kras G12A Mutations Scorpion® Kras mutation detection PCR reactions to detect Kras Exon 4 were performed on positive and negative controls (FIG. 4(a)). Scorpion® Kras mutation detection PCR reactions to detect Kras G12A mutations were performed on positive and negative controls (FIG. 4(b)). As is shown in FIG. 4, the positive controls can be detected and the negative controls cannot.

Example 3: DNase Pre-Treatment in Method of Analyzing Kras Exon 4 in RNA and DNA Associated with Microvesicles Isolated from Serum and Plasma Samples Following proper protocols, serum and plasma samples were obtained for the following analysis, from a patient diagnosed with colorectal cancer and having a Kras G12A mutation, confirmed by pathology evaluation of a biopsy.

Figure 5A:
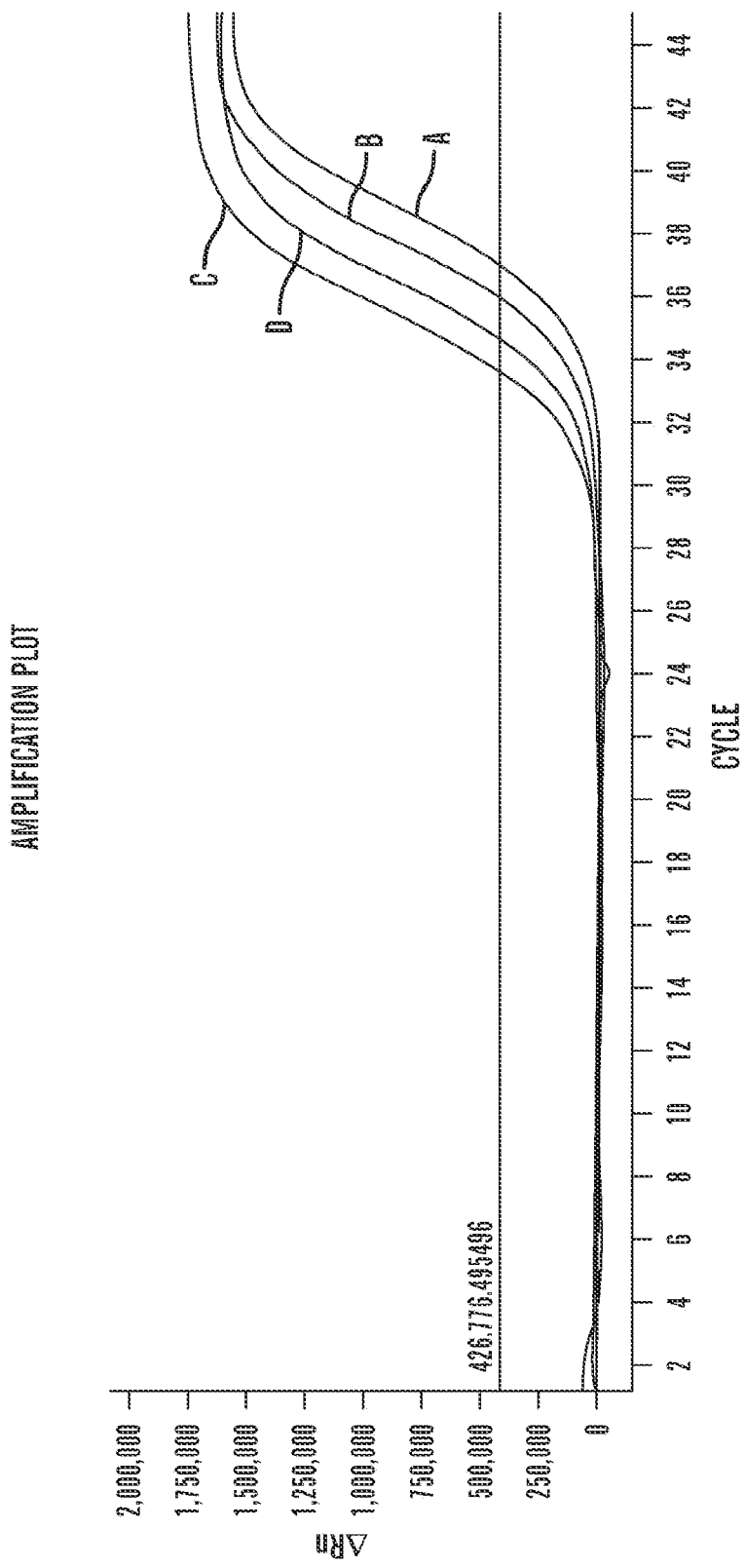
FIG. 5(a). Illustration of a result detecting Kras Exon 4 using a modified Scorpion® mutation detection method. The PCR cycle number is shown on the x-axis and the ARn (normalized fluorescence emission) versus cycle on the y-axis. The Applied Biosystems 7500 Fast qPCR machine was used for the analysis (run in standard mode, as recommended by the kit manufacturer, DxS). The labels are as follows:
  A refers to plasma exosome RNA, no DNase treatment.
  B refers to plasma exosome RNA, with DNase treatment on the outside of the exosome.
  C refers to serum exosome RNA, no DNase treatment.
  D refers to serum exosome RNA, with DNase treatment on the outside of the exosome.
Figure 5B:
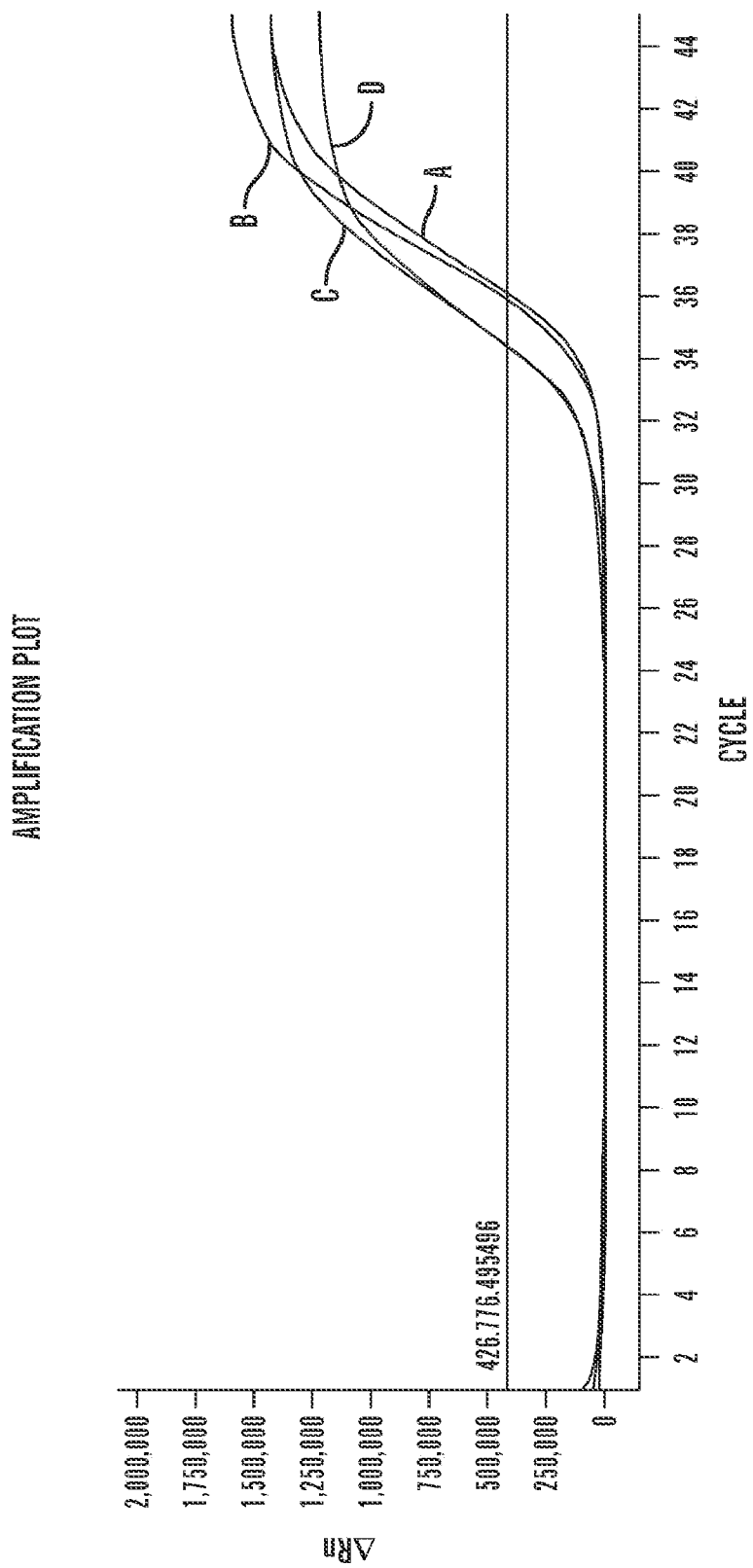
FIG. 5(b). Illustration of a result detecting Kras Exon 4 using a modified Scorpion® mutation detection method. The PCR cycle number is shown on the x-axis and the ARn (normalized fluorescence emission) versus cycle on the y-axis. The Applied Biosystems 7500 Fast qPCR machine was used for the analysis (run in standard mode, as recommended by the kit manufacturer, DxS). The labels are as follows:
  A refers to plasma exosome DNA, no DNase treatment.
  B refers to plasma exosome DNA, with DNase treatment on the outside of the exosome.
  C refers to serum exosome DNA, no DNase treatment.
  D refers to serum exosome DNA, with DNase treatment on the outside of the exosome.

Microvesicles were isolated as described previously in Example 1. Prior to isolation of nucleic acids from the microvesicles, a subset of the isolated microvesicles was pre-treated with DNase (Turbo™ DNase (Ambion®)) in order to eliminate or substantially eliminate any DNA located on the surface of the microvesicles or outside of the microvesicles. The remaining subset of microvesicles was left untreated. Samples of nucleic acid (both RNA and DNA) were obtained for analysis as described previously in Example 1. The RNA was reverse-transcribed into cDNA, as described in Example 1. The purified cDNA (FIG. 5(a)) and DNA (FIG. 5(b)) were used in Scorpion® Kras mutation detection PCR reactions to detect Kras Exon 4 (Note: the Ct values between the RNA-reverse-transcribed cDNA and the DNA cannot be directly compared since the RNA becomes diluted in the cDNA reaction and subsequent purification). As can be seen in FIGS. 5(a) and (b), the Scorpion® Kras mutation detection PCR reactions were able to successfully detect Kras Exon 4 in DNA obtained directly from microvesicles, as well as from RNA-reverse-transcribed cDNA, whether or not the microvesicles were pre-treated with DNase. As can also be seen in FIGS. 5(a) and (b), plasma RNA and DNA containing Kras Exon 4 were more abundant in the samples that came from microvesicles that were optionally pre-treated with DNase, than those that came from untreated microvesicles. These findings suggest that the DNase pre-treatment may have the effect of eliminating DNA associated with the microvesicles that might otherwise contaminate the subsequent PCR reaction, and thereby enrich for mutant nucleic acids.

Example 4: DNase Pre-Treatment in Method of Analyzing the Kras G12A Mutation in RNA and DNA Using Microvesicles Isolated from Serum and Plasma Samples, Treated with DNase Following proper protocols, serum and plasma samples were obtained for the following analysis, from the same patient as in Example 3, diagnosed with colorectal cancer and having a Kras G12A mutation, confirmed by pathology evaluation of a biopsy.

Figure 6A:
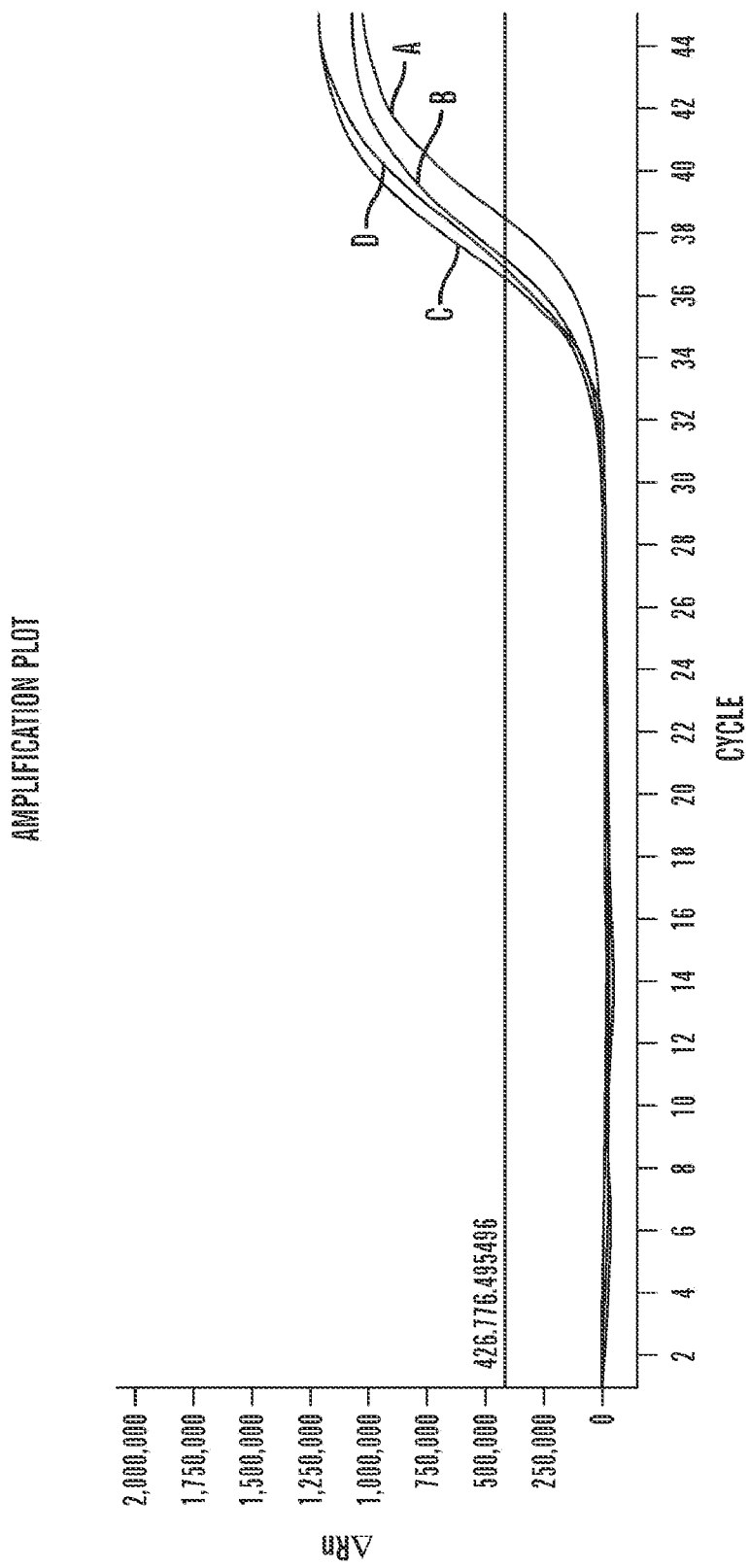
FIG. 6(a). Illustration of a result detecting Kras G12A mutation using a modified Scorpion® mutation detection method. The PCR cycle number is shown on the x-axis and the ARn (normalized fluorescence emission) versus cycle on the y-axis. The Applied Biosystems 7500 Fast qPCR machine was used for the analysis (run in standard mode, as recommended by the kit manufacturer, DxS). The labels are as follows:
  A refers to plasma exosome RNA, no DNase treatment.
  B refers to plasma exosome RNA, with DNase treatment on the outside of the exosome.
  C refers to serum exosome RNA, no DNase treatment.
  D refers to serum exosome RNA, with DNase treatment on the outside of the exosome.
Figure 6B:
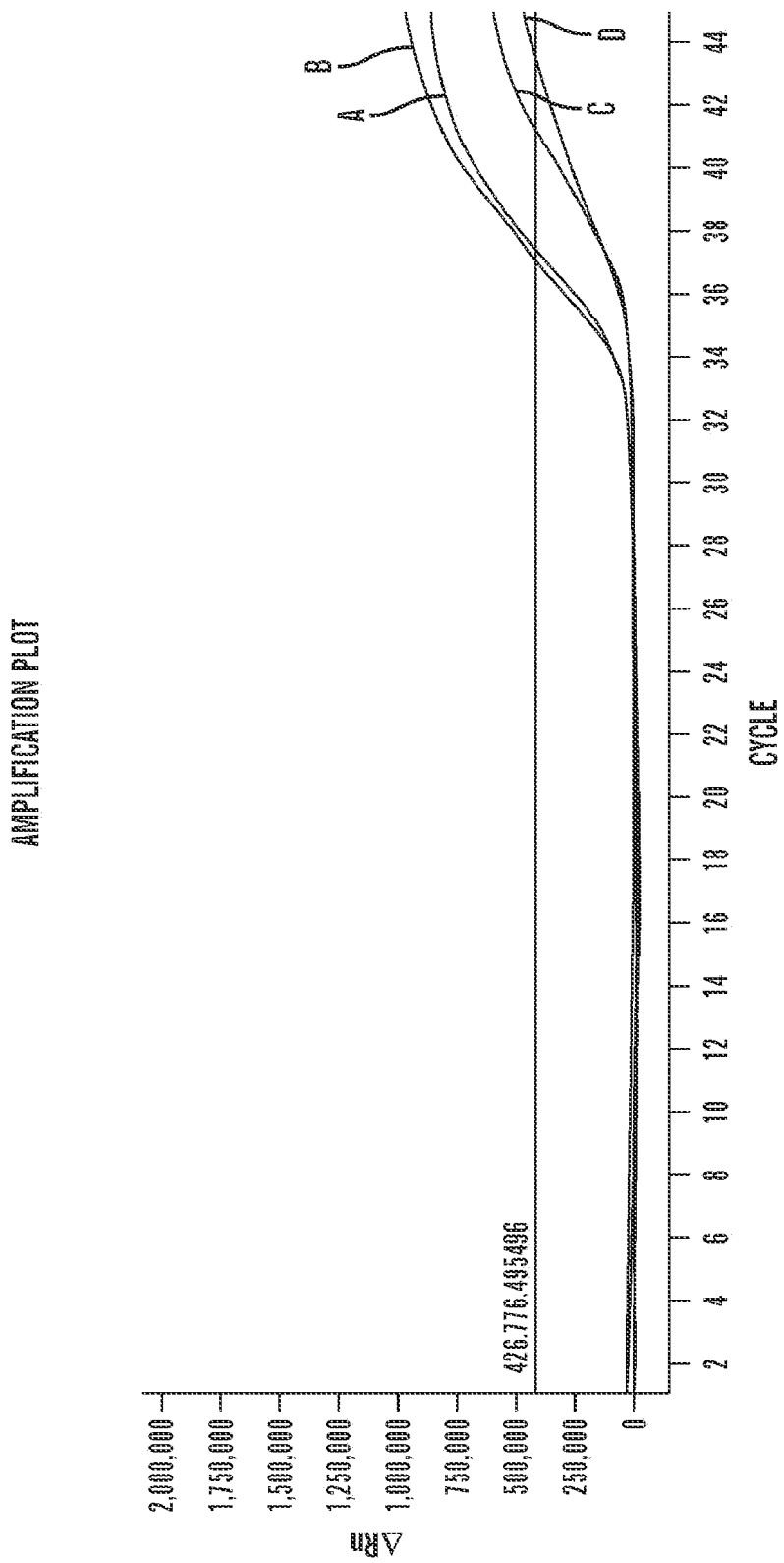
FIG. 6(b). Illustration of a result detecting Kras G12A mutation using a modified Scorpion® mutation detection method. The PCR cycle number is shown on the x-axis and the ΔRn (normalized fluorescence emission) versus cycle on the y-axis. The Applied Biosystems 7500 Fast qPCR machine was used for the analysis (run in standard mode, as recommended by the kit manufacturer, DxS). The labels are as follows.

Microvesicles were isolated as described previously in Example 1, and were either subjected to pre-treatment with DNase or left untreated, as described previously in Example 3. Samples of RNA and DNA were obtained for analysis as described previously in Example 1 and Example 2, respectively. RNA was subsequently transcribed into cDNA, as described in Example 1. The purified cDNA (FIG. 6(a)) and DNA (FIG. 6(b)) were used in Scorpion® Kras mutation detection PCR reactions to detect Kras G12A mutations. As can be seen in FIGS. 6(a) and (b), the Scorpion® Kras mutation detection PCR reactions were able to successfully detect the Kras G12A mutant in DNA obtained directly from microvesicles, as well as from RNA-reverse-transcribed cDNA, whether or not the microvesicles were pre-treated with DNase. As can also be seen in FIGS. 6(a) and (b), plasma RNA and DNA containing the Kras G12A mutation were more abundant in the samples that came from microvesicles that were pre-treated with DNase, than those that came from untreated microvesicles, supporting the suggestion that DNase pre-treatment has the potential to eliminate DNA associated with the microvesicles that might otherwise contaminate the subsequent PCR reaction, and thereby enrich for mutant nucleic acids.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

REFERENCES

1. Abravaya, K., et al. (1995). "Detection of point mutations with a modified ligase chain reaction (Gap-LCR)." *Nucleic Acids Res* 23(4): 675-82.
2. Al-Nedawi, et al. (2008). "Intercellular transfer of the oncogenic receptor EGFRvIII by microvesicles derived from tumour cells." *Nat Cell Biol* 10(5): 619-24.
3. Balzar, M., et al. (1999). "The biology of the 17-1A antigen (Ep-CAM)." *J Mol Med* 77(10): 699-712.
4. Bachireddy, P. et al. (2005). "Getting at MYC through RAS." Clin. Cancer Res. 11(12):4278-4281.
5. Bossi, A., et al. (2007). "Molecularly imprinted polymers for the recognition of proteins: the state of the art." *Biosens Bioelectron* 22(6): 1131-7.
6. Cheruvanky, A., et al. (2007). "Rapid isolation of urinary exosomal biomarkers using a nanomembrane ultrafiltration concentrator." *Am J Physiol Renal Physiol* 292(5): F1657-61.
7. Cotton, R. G., et al. (1988). "Reactivity of cytosine and thymine in single-base-pair mismatches with hydroxylamine and osmium tetroxide and its application to the study of mutations." *Proc Natl Acad Sci USA* 85(12): 4397-401.
8. Diehl, F. et al. (2008). "Circulating mutant DNA to assess tumor dynamics." Nat. Med. 14: 985-90.
9. Fiorentino, F., et al. (2003). "The minisequencing method: an alternative strategy for preimplantation genetic diagnosis of single gene disorders." *Mol Hum Reprod* 9(7): 399-410.
10. Fischer, S. G. and L. S. Lerman (1979). "Length-independent separation of DNA restriction fragments in two-dimensional gel electrophoresis." *Cell* 16(1): 191-200.
11. Fischer, S. G. and L. S. Lerman (1979). "Two-dimensional electrophoretic separation of restriction enzyme fragments of DNA." *Methods Enzymol* 68: 183-91.
12. Fumari, F. B., et al. (2007). "Malignant astrocytic glioma: genetics, biology, and paths to treatment." *Genes Dev* 21(21): 2683-710.
13. Geiss, G. K., et al. (2008). "Direct multiplexed measurement of gene expression with color-coded probe pairs." *Nat Biotechnol* 26(3): 317-25.
14. Gormally. E. et al. (2007). "Circulating free DNA in plasma or serum as biomarker of carcinogenesis: practical aspects and biological significance." Mutat. Res. 635:105-17.
15. Guatelli, J. C., et al. (1990). "Isothermal, in vitro amplification of nucleic acids by a multienzyme reaction modeled after retroviral replication." *Proc Natl Acad Sci USA* 87(5): 1874-8.
16. Hahn, P. J. (1993). "Molecular biology of double-minute chromosomes." *Bioessays* 15(7): 477-84.
17. Jancik, S., et al. (2010). "Clinical Relevance of KRAS in Human Cancers." J. Biomed. Biotech. 2010: 1-13.
18. Johnson, S., et al. (2008). "Surface-immobilized peptide aptamers as probe molecules for protein detection." *Anal Chem* 80(4): 978-83.
19. Jones, S., et al. (2008). "Core Signaling Pathways in Human Pancreatic Cancers Revealed by Global Genomic Analyses." *Science*.
20. Kan, Y. W. and A. M. Dozy (1978). "Antenatal diagnosis of sickle-cell anaemia by D.N.A. analysis of amniotic-fluid cells." *Lancet* 2(8096): 910-2.
21. Kan, Y. W. and A. M. Dozy (1978). "Polymorphism of DNA sequence adjacent to human beta-globin structural gene: relationship to sickle mutation." *Proc Natl Acad Sci USA* 75(11): 5631-5.
22. Keller, S., et al. (2007). "CD24 is a marker of exosomes secreted into urine and amniotic fluid." *Kidney Int* 72(9): 1095-102.
23. Kwoh, D. Y., et al. (1989). "Transcription-based amplification system and detection of amplified human immunodeficiency virus type 1 with a bead-based sandwich hybridization format." *Proc Natl Acad Sci USA* 86(4): 1173-7.
24. Landegren, U., et al. (1988). "A ligase-mediated gene detection technique." *Science* 241(4869): 1077-80.
25. Li, J., et al. (2008). "Replacing PCR with COLD-PCR enriches variant DNA sequences and redefines the sensitivity of genetic testing." *Nat Med* 14(5): 579-84.
26. Liu, Q., et al. (2006). "Reconstitution, activities, and structure of the eukaryotic RNA exosome." *Cell* 127(6): 1223-37.
27. McLendon, R., et al. (2008). "Comprehensive genomic characterization defines human glioblastoma genes and core pathways." *Nature*.
28. Miele, E. A., et al. (1983). "Autocatalytic replication of a recombinant RNA." *J Mol Biol* 171(3): 281-95.
29. Miranda, K. C., et al. 2010. Nucleic acids within urinary exosomes/microvesicles are potential biomarkers for renal disease. *Kidney Int.* 78:191-9.
30. Myers, R. M., et al. (1985). "Detection of single base substitutions by ribonuclease cleavage at mismatches in RNA:DNA duplexes." *Science* 230(4731): 1242-6.
31. Nagrath, S., et al. (2007). "Isolation of rare circulating tumour cells in cancer patients by microchip technology." *Nature* 450(7173): 1235-9.
32. Nakazawa, H., et al. (1994). "UV and skin cancer: specific p53 gene mutation in normal skin as a biologically relevant exposure measurement." *Proc Natl Acad Sci USA* 91(1): 360-4.
33. Orita, M., et al. (1989). "Detection of polymorphisms of human DNA by gel electrophoresis as single-strand conformation polymorphisms." *Proc Natl Acad Sci USA* 86(8): 2766-70.
34. Parsons, D. W., et al. (2008). "An Integrated Genomic Analysis of Human Glioblastoma Multiforme." *Science*.
35. Quest Diagnostics, KRAS Mutation Analysis, Reference Materials (taken from last visited Sep. 9, 2010).
36. Raposo, G., et al. (1996). "B lymphocytes secrete antigen-presenting vesicles." *J Exo Med* 183(3): 1161-72.
37. Russo, et al., (2010). International Patent Application No. PCT/US10/042365.
38. Skog, J., et al. (2009). "Use of Microvesicles in Diagnosis, Prognosis and Treatment of Medical Diseases and Conditions." International Patent Publication No. WO 2009/100029.

39. Steemers, F. J., et al. (2006). "Whole-genome genotyping with the single-base extension assay." *Nat Methods* 3(1): 31-3.
40. Taylor, D. D. and C. Gercel-Taylor (2008). "MicroRNA signatures of tumor-derived exosomes as diagnostic biomarkers of ovarian cancer." *Gynecol Oncol* 110(1): 13-21.
41. van Dijk, E. L., et al. (2007). "Human cell growth requires a functional cytoplasmic exosome, which is involved in various mRNA decay pathways." *RNA* 13(7): 1027-35.
42. Went, P. T., et al. (2004). "Frequent EpCam protein expression in human carcinomas." *Hum Pathol* 35(1): 122-8.
43. Wood, L. D., et al. (2007). "The genomic landscapes of human breast and colorectal cancers." *Science* 318(5853): 1108-13.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method for identifying the presence or absence of a Kras genetic aberration in a microvesicle from a subject, wherein the Kras genetic aberration encodes a Kras mutation selected from the group consisting of G12A, G12D, G12R, G12C, G12S, and G12V, the method comprising the steps:
    a) isolating one or more microvesicles from a body fluid of a subject after by filtering the body fluid sample to remove cell contamination;
    b) removing DNA located outside the one or more microvesicles;
    c) extracting DNA and/or RNA from the one or more microvesicles; and
    d) identifying the presence or absence of the Kras genetic aberration in the extracted DNA and/or RNA by:
        i) sequencing nucleic acids encoding Kras present in the extracted DNA and/or RNA to thereby identify the presence or absence of the Kras genetic aberration;
        ii) performing allele specific amplification of one or more nucleic acids encoding the Kras mutation on the extracted DNA and/or RNA, and comparing resulting amplification products to those of an appropriate control to thereby identify the presence or absence of the Kras genetic aberration; and/or
        iii) hybridizing probes specific for nucleic acid encoding the Kras mutation to the extracted DNA and/or RNA and detection of probes specifically hybridized to the extracted DNA and/or RNA, as compared to that of an appropriate control, to thereby identify the presence or absence of the Kras genetic aberration.

2. The method of claim 1, wherein the microvesicles are treated with DNase prior to extracting step b) to eliminate DNA located outside of the microvesicles.

3. The method of claim 1, wherein the body fluid is blood, plasma, serum, urine, or combinations thereof.

4. The method of claim 1, wherein the microvesicles are enriched for those originating from a specific cell type.

5. The method of claim 4, wherein the specific cell type is lung, pancreas, stomach, intestine, bladder, kidney, ovary, testis, skin, colorectal, breast, prostate, brain, esophagus, liver, placenta, or fetus cells.

6. The method of claim 4, wherein a microvesicular surface molecule is used to enrich for microvesicles from a specific cell type.

7. The method of claim 6, wherein the microvesicular surface molecule is a surface antigen associated with tumor cells.

8. The method of claim 6, wherein the microvesicular surface molecule is epithelial-cell-adhesion-molecule (EpCAM), CD24, CD7-, carcinoembryonic antigen (CEA), EGFR, EGFRvIII, Fas ligand, TRAIL, transferrin receptor, p38.5, p97, or HSP72.

9. The method of claim 4, wherein the absence of a microvesicular surface molecule is used to enrich for microvesicles from a specific cell type.

10. The method of claim 9, wherein the surface molecule is CD80 or CD86.

11. The method of claim 4, wherein the microvesicles are enriched using antibodies, aptamers, aptamer analogs, or molecularly imprinted polymers.

12. The method of claim 1, wherein both DNA and RNA are extracted.

13. The method of claim 12, wherein both DNA and RNA are analyzed.

14. The method of claim 1, wherein the RNA is reverse-transcribed into complementary DNA.

15. The method of claim 1, wherein the extracted DNA and/or RNA is amplified prior to identifying step d).

16. The method of claim 15, wherein amplifying is by polymerase chain reaction (PCR), in situ PCR, quantitative PCR, nested PCR, self-sustained sequence replication, transcriptional amplification system reaction, cold-PCR or any combination thereof.

17. The method of claim 1, wherein the subject is a human colorectal cancer patient.

18. A method for treating colorectal cancer in a subject, comprising:
    a) isolating one or more microvesicles from a serum or plasma sample from the subject after filtering the sample to remove any cell contamination;
    b) removing DNA located outside the one or more microvesicles;
    c) extracting DNA and/or RNA from the microvesicles;
    d) analyzing the DNA and/or RNA contained within the isolated microvesicles for the presence or absence of a Kras genetic aberration selected from the group consisting of G12A, G12D, G12R, G12C, G12S, and G12V; and
    e) treating the subject with chemotherapy and withholding treatment with an EGFR targeting treatment therapy if the presence of the Kras genetic aberration is identified or treating the subject with an EGFR targeting treatment and withholding chemotherapy if the absence of the Kras genetic aberration is identified.

19. The method of claim 18, wherein analyzing comprises reverse transcribing RNA into cDNA and purifying by a 30 kDa microcolumn, and then detecting Kras Exon 4 mutations by PCR.

20. The method of claim 18, wherein the microvesicles are treated with DNase prior to analysis to eliminate DNA located outside of the microvesicles.

21. The method of claim 18, wherein the microvesicles are enriched for those originating from a specific cell type.

22. The method of claim 21, wherein the specific cell type is lung, pancreas, stomach, intestine, bladder, kidney, ovary, testis, skin, colorectal, breast, prostate, brain, esophagus, liver, placenta, or fetus cells.

23. The method of claim 21, wherein a microvesicular surface molecule is used to enrich for microvesicles from a specific cell type.

24. The method of claim 23, wherein the microvesicular surface molecule is a surface antigen associated with tumor cells.

25. The method of claim 23, wherein the microvesicular surface molecule is epithelial-cell-adhesion-molecule (Ep-CAM), CD24, CD7-, carcinoembryonic antigen (CEA), EGFR, EGFRvIII, Fas ligand, TRAIL, transferrin receptor, p38.5, p97, or HSP72.

26. The method of claim 21, wherein the absence of a microvesicular surface molecule is used to enrich for microvesicles from a specific cell type.

27. The method of claim 26, wherein the surface molecule is CD80 or CD86.

28. The method of claim 21, wherein the microvesicles are enriched using antibodies, aptamers, aptamer analogs, or molecularly imprinted polymers.

29. The method of claim 18, wherein both DNA and RNA are extracted.

30. The method of claim 29, wherein both DNA and RNA are analyzed.

31. The method of claim 18, wherein the RNA is reverse-transcribed into complementary DNA.

32. The method of claim 18, wherein the RNA and/or DNA is analyzed directly without an amplification step.

33. The method of claim 18, wherein the RNA and/or DNA is amplified prior to analysis.

34. The method of claim 33, wherein amplifying the RNA and/or DNA comprises performing a polymerase chain reaction (PCR), in situ PCR, quantitative PCR, nested PCR, self-sustained sequence replication, transcriptional amplification system reaction, cold-PCR or any combination thereof.

35. The method of claim 18, wherein analyzing comprises sequencing the extracted DNA and/or RNA.

36. A method for identifying the presence or absence of a Kras genetic aberration in a microvesicle from a subject, wherein the Kras genetic aberration encodes a Kras mutation selected from the group consisting of G12A, G12D, G12R, G12C, G12S, and G12V, the method comprising the steps:

a) isolating one or more microvesicles from a body fluid of a subject after filtering the body fluid sample to remove cell contamination;
b) extracting DNA and/or RNA from the one or more microvesicles; and
c) identifying the presence or absence of the Kras genetic aberration in the extracted DNA and/or RNA by:
  i) sequencing nucleic acids encoding Kras present in the extracted DNA and/or RNA to thereby identify the presence or absence of the Kras genetic aberration;
  ii) performing allele specific amplification of one or more nucleic acids encoding the Kras mutation on the extracted DNA and/or RNA, and comparing resulting amplification products to those of an appropriate control to thereby identify the presence or absence of the Kras genetic aberration; and/or
  iii) hybridizing probes specific for nucleic acid encoding the Kras mutation to the extracted DNA and/or RNA and detection of probes specifically hybridized to the extracted DNA and/or RNA, as compared to that of an appropriate control, to thereby identify the presence or absence of the Kras genetic aberration.

37. A method for treating colorectal cancer in a subject, comprising:
a) isolating one or more microvesicles from a serum or plasma sample from the subject after filtering the sample to remove any cell contamination;
b) analyzing the DNA and/or RNA contained within the isolated microvesicles for the presence or absence of a Kras genetic aberration selected from the group consisting of G12A, G12D, G12R, G12C, G12S, and G12V; and
c) treating the subject with chemotherapy and withholding treatment with an EGFR targeting treatment therapy if the presence of the Kras genetic aberration is identified, and treating the subject with an EGFR targeting treatment and withholding chemotherapy if the absence of the Kras genetic aberration is identified.

* * * * *